(12) United States Patent
Michaels et al.

(10) Patent No.: US 8,942,935 B2
(45) Date of Patent: Jan. 27, 2015

(54) CHARGE LEVEL MEASUREMENT

(75) Inventors: Matthew J. Michaels, St. Francis, MN (US); Joel A. Anderson, Brooklyn Park, MN (US); Douglas S. Cerny, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1031 days.

(21) Appl. No.: 12/815,095

(22) Filed: Jun. 14, 2010

(65) Prior Publication Data

US 2011/0307033 A1  Dec. 15, 2011

(51) Int. Cl.
*A61N 1/08* (2006.01)
*A61N 1/37* (2006.01)
*G01R 31/36* (2006.01)
*A61N 1/378* (2006.01)

(52) U.S. Cl.
CPC .......... *A61N 1/3708* (2013.01); *G01R 31/3606* (2013.01); *A61N 1/378* (2013.01)
USPC .............................................. 702/63; 607/60

(58) Field of Classification Search
CPC ........... G01R 31/3624; G01R 31/3606; A61N 1/3708
USPC ......................................................... 702/63
See application file for complete search history.

(56) References Cited

U.S. PATENT DOCUMENTS

| | | |
|---|---|---|
| 4,556,061 A | 12/1985 | Barreras et al. |
| 5,137,020 A | 8/1992 | Wayne et al. |
| 5,325,041 A | 6/1994 | Briggs |
| 5,344,431 A | 9/1994 | Merritt et al. |
| 5,369,364 A | 11/1994 | Renirie et al. |
| 5,391,193 A | 2/1995 | Thompson |
| 5,769,873 A | 6/1998 | Zadeh |
| 6,016,448 A | 1/2000 | Busacker et al. |
| 6,108,579 A | 8/2000 | Snell et al. |
| 6,141,583 A | 10/2000 | Pape et al. |
| 6,191,557 B1 | 2/2001 | Gray et al. |
| 6,198,253 B1 | 3/2001 | Kurle et al. |
| 6,366,809 B1 | 4/2002 | Olson et al. |
| 6,400,988 B1 | 6/2002 | Gurewitsch |
| 6,534,954 B1 * | 3/2003 | Plett .............................. 320/132 |

(Continued)

FOREIGN PATENT DOCUMENTS

| | | |
|---|---|---|
| EP | 0160801 A2 | 11/1985 |
| WO | 0105466 A1 | 1/2001 |

(Continued)

OTHER PUBLICATIONS

Welch "An Introduction to the Kalman Filter", Jul. 2006, UNC-Chapel Hill, TR 95-041, http://www.cs.unc.edu/~welch/media/pdf/kalman_intro.pdf.*

(Continued)

*Primary Examiner* — Jonathan C Teixeira Moffat
*Assistant Examiner* — Regis Betsch
(74) *Attorney, Agent, or Firm* — Shumaker & Sieffert, P.A.

(57) ABSTRACT

This disclosure describes techniques for estimating an amount of charge on a power source. A processor may determine an uncertainty value associated with a first charge level of a power source and an uncertainty value associated with a second charge level of the power source. Based on the uncertainties, the processor may adjust the first charge level to generate an adjusted charge level. The processor may further adjust the adjusted charge level based on the behavior of the power source.

28 Claims, 11 Drawing Sheets

(56) References Cited

U.S. PATENT DOCUMENTS

| | | |
|---|---|---|
| 6,584,355 B2 | 6/2003 | Stessman |
| 6,648,823 B2 | 11/2003 | Thompson |
| 6,671,552 B2 | 12/2003 | Merritt et al. |
| 6,748,273 B1 | 6/2004 | Obel et al. |
| 6,820,019 B1 | 11/2004 | Kelly et al. |
| 6,885,894 B2 | 4/2005 | Stessman |
| 6,901,293 B2 | 5/2005 | Rogers et al. |
| 7,123,964 B2 | 10/2006 | Betzold et al. |
| 7,142,923 B2 | 11/2006 | North et al. |
| 7,167,756 B1 | 1/2007 | Torgerson et al. |
| 7,177,690 B2 | 2/2007 | Woods et al. |
| 7,191,005 B2 | 3/2007 | Stessman |
| 7,194,308 B2 | 3/2007 | Krig et al. |
| 7,215,999 B1 | 5/2007 | Shahandeh et al. |
| 7,221,977 B1 | 5/2007 | Weaver et al. |
| 7,239,146 B2 | 7/2007 | James et al. |
| 7,450,991 B2 | 11/2008 | Smith et al. |
| 7,469,161 B1 | 12/2008 | Gandhi et al. |
| 7,542,801 B2 | 6/2009 | Rogers et al. |
| 7,711,426 B2 | 5/2010 | Armstrong et al. |
| 8,108,160 B2 * | 1/2012 | Liu et al. .......... 702/63 |
| 8,116,998 B2 * | 2/2012 | Hess .......... 702/63 |
| 2003/0065366 A1 | 4/2003 | Merritt et al. |
| 2004/0039424 A1 | 2/2004 | Merritt et al. |
| 2005/0102005 A1 | 5/2005 | Krig et al. |
| 2005/0177206 A1 | 8/2005 | North et al. |
| 2005/0277994 A1 | 12/2005 | McNamee et al. |
| 2006/0100833 A1 * | 5/2006 | Plett .......... 703/2 |
| 2006/0111854 A1 | 5/2006 | Plett |
| 2006/0111870 A1 * | 5/2006 | Plett .......... 702/181 |
| 2006/0212277 A1 | 9/2006 | Hansen et al. |
| 2007/0150018 A1 | 6/2007 | Betzold et al. |
| 2007/0179547 A1 | 8/2007 | Armstrong et al. |
| 2007/0179548 A1 | 8/2007 | Armstrong et al. |
| 2007/0179549 A1 | 8/2007 | Russie |
| 2008/0097544 A1 * | 4/2008 | Gandhi et al. .......... 607/29 |
| 2008/0177345 A1 | 7/2008 | Schmidt et al. |
| 2008/0306569 A1 | 12/2008 | Tobacman |
| 2009/0099625 A1 | 4/2009 | Crowley et al. |
| 2009/0182517 A1 | 7/2009 | Gandhi et al. |
| 2009/0276015 A1 | 11/2009 | Rondoni et al. |
| 2010/0076704 A1 * | 3/2010 | Liu et al. .......... 702/63 |
| 2011/0031938 A1 * | 2/2011 | Ishikawa .......... 320/162 |
| 2011/0133690 A1 * | 6/2011 | Crane .......... 320/107 |

FOREIGN PATENT DOCUMENTS

| | | |
|---|---|---|
| WO | 0249718 A1 | 6/2002 |
| WO | 2004091697 A1 | 10/2004 |
| WO | 2008038202 A2 | 4/2008 |
| WO | 2009055203 A1 | 4/2009 |
| WO | 2009078905 A1 | 6/2009 |
| WO | 2009091407 A2 | 7/2009 |
| WO | 2009134473 A1 | 10/2010 |

OTHER PUBLICATIONS

Maybeck, Stoichastic models, estimation and control, 1979, vol. 1, Chapter 1, Academy Press.*

Notification of Transmittal of the International Search Report and the Written Opinion of the International Searching Authority for patent application No. PCT/US2010/046152, mailed Feb. 18, 2011, 12 pages.

U.S. Appl. No. 12/771,475, filed Apr. 30, 2010, Davis at al.

Battery and Energy Technologies, State of Charge (SOC) Determination, Electropedia, 2005, 6 pages.

Office Action for U.S. Appl. No. 12/771,475, mailed Oct. 26, 2012, 7 pages.

Response to Office Action for U.S. Appl. No. 12/771,475, filed Jan. 28, 2013, 15 pages.

Response to Final Office Action dated Dec. 17, 2013, from U.S. Appl. No. 12/771,475, filed Feb. 12, 2014, 16 pp.

Office Action from U.S. Appl. No. 12/771,475, dated Dec. 17, 2013, 9 pp.

Office Action from U.S. Appl. No. 12/771,475, dated Jul. 31, 2014, 9 pp.

Response to Final Office Action dated Dec. 17, 2013 and the Advisory Action dated Apr. 3, 2014, from U.S. Appl. No. 12/771,475, filed May 5, 2014, 16 pp.

* cited by examiner

CHARGE LEVEL MEASUREMENT

TECHNICAL FIELD

This disclosure is directed to techniques for power management in a device and, more particularly, measurement of battery longevity in the device.

BACKGROUND

Devices often make use of one or more rechargeable or non-rechargeable power sources, such as batteries, to provide operating power to circuitry of the device. During operation, the charge level of a power source drops due to power consumption by the device. The device may provide some indication of remaining charge as the power source drains, e.g., as the battery or batteries drain. A user of the device may utilize the remaining charge indication to determine whether the power source needs to be replaced or recharged. By replacing or recharging the power source before the charge on the power source is fully depleted, the user can ensure that operation of the device will not be interrupted, or otherwise adversely impacted, due to power source depletion.

SUMMARY

In general, this disclosure describes techniques for estimating a charge level of a power source associated with a device. One example of the device includes a medical device such as an programmer for an implantable medical device (IMD) and the IMD itself. Aspects of this disclosure are described in the context of the device being a medical device. However, aspects of this disclosure are not limited to medical devices.

The power source may power electronic circuitry within the medical device. In some examples, a processor may compare uncertainty values associated with different types of power source charge level estimation techniques. Based on the comparison, the processor may adjust an estimated charge level to provide a better estimate of the charge level of the power source associated with the medical device.

In some examples, a processor may also monitor changes in one or more characteristics of a power source. The processor may adjust the estimated power source charge level based on the changes in the one or more characteristics of the power source.

In one example, aspects of this disclosure are directed to a method comprising determining, with a processor associated with a medical device, a first uncertainty value associated with a first charge level estimate of a power source and a second uncertainty value associated with a second charge level estimate of the power source, and adjusting, with the processor, the first charge level estimate based on at least the first and second uncertainty values to generate an adjusted charge level estimate.

In another example, aspects of this disclosure are directed to a medical device system comprising a power source, and a processor configured to determine a first uncertainty value associated with a first charge level estimate of the power source and a second uncertainty value associated with a second charge level estimate of the power source, and adjust the first charge level estimate based on at least the first and second uncertainty values to generate an adjusted charge level estimate.

In another example, aspects of this disclosure are directed to a non-transitory computer-readable storage medium comprising instructions that cause one or more processors in a medical device to determine a first uncertainty value associated with a first charge level estimate of a power source and a second uncertainty value associated with a second charge level estimate of the power source, and adjust the first charge level estimate based on at least the first and second uncertainty values to generate an adjusted charge level estimate.

In another example, aspects of this disclosure are directed to a medical device system comprising means for determining a first uncertainty value associated with a first charge level estimate of a power source and a second uncertainty value associated with a second charge level estimate of the power source, and means for adjusting the first charge level estimate based on at least the first and second uncertainty values to generate an adjusted charge level estimate, wherein at least one of the means for determining and the means for adjusting is implemented at least partially as hardware.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
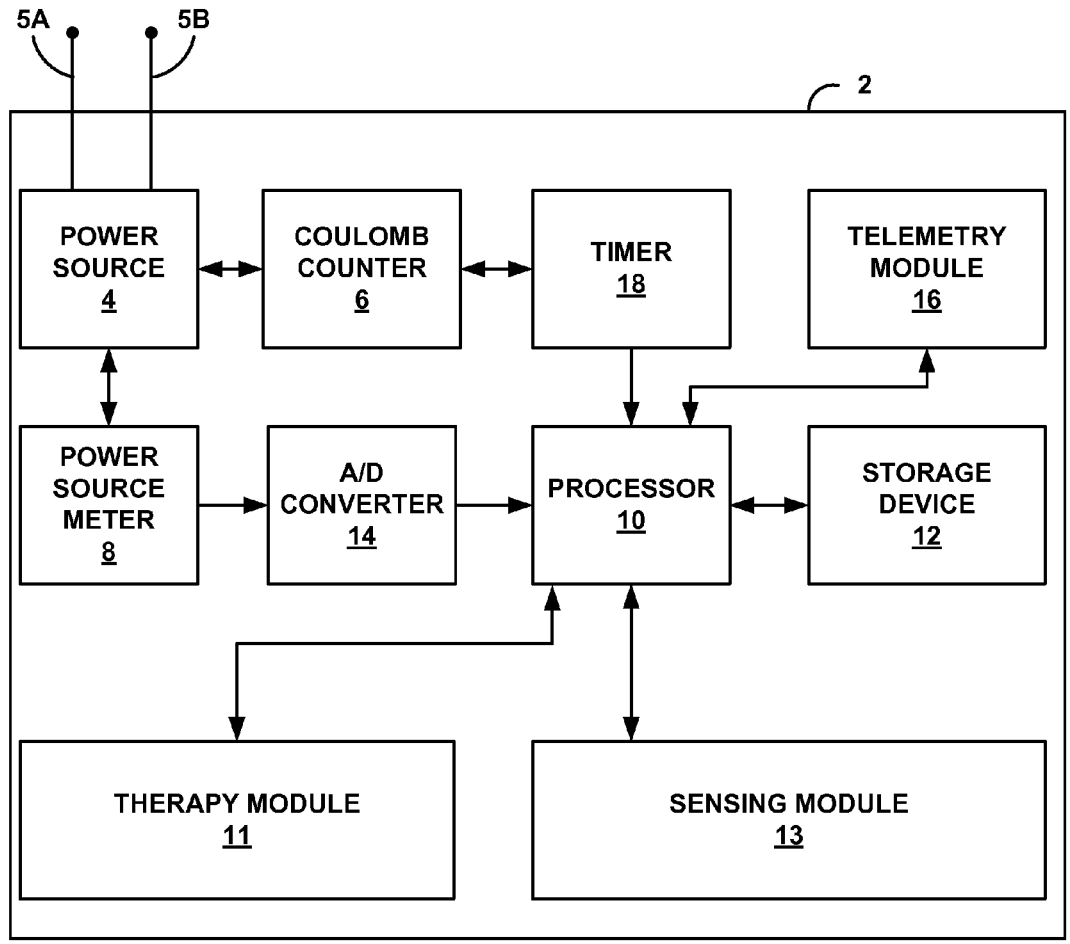
FIG. 1 is a block diagram illustrating an example device that may be configured to estimate a charge level of a power source in a device.

Various aspects of this disclosure relate to providing an estimate of charge levels for a power source associated with a device, such as a medical device including an implantable medical device (IMD). Although aspects of this disclosure are described in the context of medical devices for purposes of illustration, aspects of this disclosure are not limited to medical devices. Many devices often make use of one or more rechargeable or non-rechargeable power sources, such as batteries, to provide operating power to device circuitry. During operation, the charge level of such a power source drops due to power consumption by the device. The charge level estimate, of the power source, may indicate the amount of remaining charge on the power source. The amount of remaining charge may be indicated in terms of units of charge, percentage of full charge, fraction of full charge, remaining operating time before full depletion, or any other representations.

In some aspects of this disclosure, a processor may derive an estimation of the charge level, of the power source, from a coulomb counter. The coulomb counter may count the amount of charge delivered by the power source, e.g., battery, and in some instances, the amount of charge received by the power source, e.g., when the battery is being recharged. To count the amount of charge delivered by the power source, the coulomb counter may integrate the amount of current delivered by the power source over time. However, coulomb counters may not be completely accurate and there may be an uncertainty value associated with amount of charge delivered by the power source as measured by the coulomb counter. Accordingly, the charge level estimate derived from the coulomb counter by the processor may be an estimate of the actual charge level. The actual charge level may be within the bounds of the range of uncertainty values associated with the measurement by the coulomb counter. For example, a coulomb counter may estimate that a battery delivered 10 milliamp-Hours (mA-Hr) of charge. The uncertainty value of the estimate, i.e., margin of error, may be +/−5%. In this example, based on techniques described in more detail below, the processor may estimate that the battery charge is at 80% of full capacity. Therefore, the actual battery charge may be between 75% of full capacity and 85% of full capacity, i.e., 80−5 and 80+5.

Due to inherent drift in error of a coulomb counter, the uncertainty of the charge level estimate derived from the measurement by the coulomb counter may increase over time, e.g., the uncertainty value may increase over time. For example, the uncertainty value may be +/−1% initially and then, over time, the uncertainty value may increase to +/−20%. Therefore, over time, the charge level estimate derived from a measurement by the coulomb counter may become more and more uncertain. The changes in the uncertainty values, e.g., increase in the uncertainty value, may be modeled or approximated.

In some aspects, the processor may adjust the charge level estimate derived from the coulomb counter measurement to reduce the uncertainty of the measurement. The adjusted charge level estimate may be more accurate than the charge level estimate derived from the coulomb counter measurement. The processor may adjust the charge level estimate derived from the coulomb counter measurement based on at least one other technique to determine the charge level estimate. A non-limiting example of another technique to determine the charge level estimate may be determining the charge level estimate based on a measurement of the power source voltage. The processor may adjust the charge level estimate derived from the coulomb counter measurement based on a measurement of the power source voltage.

A power source manufacturer, e.g., a battery manufacture, or some other entity utilizing the power source, may model the relationship between the charge level and the power source voltage or some other intrinsic property. The model may indicate an estimate of how much charge is delivered for a given power source voltage as the power source discharges. As one non-limiting example, assuming the power source is a battery, the model may indicate that, at a given state of the battery life, when the battery voltage is at 3 volts, the battery charge is approximately 60% of full capacity. The state of the battery life may include the length of time the battery has been operating, the number of times that the battery has been discharged and recharged, i.e., the number of times that the battery has been cycled, and characteristics of the battery such a unit-to-unit variance in the characteristics of the battery. The state of the battery life may effect the indication of the charge level estimate relative to the battery voltage.

Like the coulomb counter, there may be an uncertainty associated with the charge level estimate derived from the power source voltage. The uncertainty value may be caused by a flat battery voltage discharge of the power source and an inexactness in the voltage measurement of the power source. Moreover, the uncertainty value may be different at different power source voltages. The model may provide the uncertainty value of the charge level estimate derived from the voltage measurement of the power source. The actual charge level may be bounded by the uncertainty value, i.e., margin of error, of the charge level estimate derived from the power source voltage. As another example, the model may indicate that, at a given state of the power source, when the power source voltage is at 3 volts, the charge level estimate is approximately 60% of full capacity. However, due to the uncertainty, the actual charge level may be between 70% and 50% of full capacity, assuming +/−10% uncertainty, i.e., 60+10 and 60−10.

As noted above, the processor may adjust the charge level estimate derived from the coulomb counter measurement based on the charge level estimate derived from the voltage measurement, as one non-limiting example. In some examples, the processor may compare the uncertainty value associated with the charge level estimate derived from the coulomb counter measurement and the uncertainty value associated with the charge level estimate derived from the power source voltage measurement. Based on the comparison, the processor may adjust the charge level estimate derived from the coulomb counter measurement. The adjustment may cause the adjusted charge level estimate to be a better approximation of the actual charge level of the power source.

It should be noted that charge level estimates derived from a coulomb counter measurement and charge level estimates derived from a power source voltage measurement are provided for example purposes only. Aspects of this disclosure are not limited to charge level estimates derived from coulomb counter and power source voltage measurements.

In some instances, instead of or in addition to deriving charge level estimates of the power source from coulomb counter measurements and power source voltage measurements, the processor may derive charge level estimates utilizing various other techniques. For example, the processor may derive charge level estimates based on a pressure of the power source, temperature of the power source, impedance of the power source, size changes in the power source, as well as other techniques. In some examples, the processor may adjust the charge level estimate derived from the coulomb counter measurement based on the charge level estimate derived from one or more of power source voltage measurement, power source pressure measurement, power source temperature measurement, power source impedance measurement, and power source size measurements, as well as other power source measurements that relate to charge level estimates.

Furthermore, although the above examples describe the processor as adjusting the charge level estimate derived from the coulomb counter measurement based on one or more other techniques to estimate the power source charge level, aspects of this disclosure are not so limited. In some examples, the processor may adjust the charge level estimate derived from techniques other than the coulomb counter measurement based on the charge level estimate derived from the coulomb counter measurement. In some examples, the processor may adjust the charge level estimate derived from techniques other than the coulomb counter measurement based on the charge level estimate derived from the coulomb counter measurement, as well as, other measurements from which the charge level estimate is derived.

Moreover, a coulomb counter may not be necessary in every example of this disclosure. In some examples, the processor may derive an estimate of the charge level of the power source based on at least one of a power source voltage measurement, power source pressure measurement, power source impedance measurement, and power source size measurement, as a few examples. The processor may then adjust the charge level estimate of the processor based on at least one other technique to estimate the charge level.

Accordingly, in general, aspects of this disclosure may relate to determining an uncertainty value associated with a first charge level estimate, of a power source, derived from any technique to estimate the charge level. Aspects of this disclosure may further relate to determining an uncertainty value associated with a second charge level estimate derived from at least one other technique to estimate the charge level. In aspects of this disclosure, a device, such as a medical device may adjust the first charge level estimate based on the uncertainties. Examples of techniques to estimate the charge level include, but are not limited to, charge level estimates derived from a coulomb counter measurement, power source voltage measurement, power source pressure measurement, power source temperature measurement, and power source size measurement.

FIG. 1 is a block diagram illustrating an example device 2 that may be configured to estimate a charge level of a power source in a device. Examples of device 2 include devices that are powered by a battery or batteries such as, but are not limited to, a medical device such as an implantable medical device (IMD), a laptop computer, a mobile phone, a gaming counsel, and the like. Aspects of this disclosure are described in the context of device 2 being an IMD, but this disclosure should not be considered limited to IMDs. Aspects of this disclosure may be utilized in any medical device including external medical devices that may provide therapy or sense one or more physiological conditions, as well as, external programmers that program other medical devices. Furthermore, aspects of this disclosure may be utilized in devices other than medical devices.

Device 2 may include power source 4, coulomb counter 6, power source meter 8, processor 10, storage device 12, analog-to-digital (A/D) converter 14, telemetry module 16, and timer 18. Although shown as separate units in FIG. 1, in some examples, coulomb counter 6, power source meter 8, A/D converter 14, and timer 18 may be incorporated as a part of processor 10. Device 2 may include additional components not shown for purposes of clarity. For example, device 2 may include a display and a user interface in examples where device 2 is a laptop computer, mobile phone, gaming counsel, and the like. As another example, device 2 may include a microphone and speaker to effectuate telephonic communication in examples where device 2 is a mobile phone. Various other components may be formed within device 2 based on the functionality of device 2. Aspects of this disclosure should not be considered limited to the example additional components described above.

In some examples, device 2 may include sensing module 13 to sense physiological signals or other parameters associated with a patient, and/or therapy module 11 to deliver therapy to a patient. Therapy module 11 and sensing module 13 are shown for illustration purposes and may not be required in every example of device 2. For example, in instances where device 2 is not configured to deliver therapy or sense patient signals, such as in examples where device 2 is an external medical device programmer, a mobile phone, a laptop, and a gaming counsel, device 2 may not include sensing module 13 and therapy module 11. Furthermore, in some examples, device 2 may include therapy module 11, but may not include sensing module 13. In some examples, device 2 may include sensing module 13, but may not include therapy module 11.

In some examples of device 2 that include therapy module 11 and sensing module 13, therapy module 11 may be coupled to one or more electrodes. In some cases, some of the electrodes may be carried on one or more leads. Therapy module 11 may be configured to provide electrical stimulation therapy to a patient to address at least one physiological condition experienced by the patient. In some examples, therapy module 11 may be a drug delivery device configured to provide medication to a patient in accordance with a drug delivery schedule. In some examples, sensing module 13 may be coupled to the same electrodes as therapy module 13 to sense physiological signals or other parameters associated with the patient. In some examples, sensing module 13 may be coupled to electrodes designated for sensing purposes that are different than the electrodes coupled to therapy module 13. In some examples, instead of or in addition to being coupled to electrodes, sensing module 13 may be coupled to different types of sensors to sense physiological signals or parameters associated with the patient. For example, sensing module 13 may be coupled to pressure sensors, blood flow sensors, respiration sensors, and the like. It should be noted that aspects of this disclosure are not limited to the example functions of therapy module 11 and sensing module 13 described above. An example of device 2 configured as an IMD is shown in more detail with respect to FIG. 11.

Power source 4 may be any unit that provides power to the components of device 2 by discharging charge that is stored on power source 4. Power source 4 may be a single battery or multiple batteries that are tied together in parallel or in series to form a single power source. Also, power source 4 may be one or more capacitors or super capacitors tied together in parallel or in series to form a single power source. In examples where device 2 includes multiple different power sources, aspects of this disclosure may be extendable to each power source. For purposes of illustration, aspects of this disclosure are described in the context of power source 4 being one or more batteries. However, aspects of this disclosure are not so limited.

Power source 4 may be a rechargeable battery or batteries or a non-rechargeable battery or batteries, e.g., one or more primary cell batteries. Power source 4 may be recharged via power terminals 5A, 5B which may be power lines that extent from device 2. In some alternate examples, power terminals 5A, 5B may comprise an inductive coil. The inductive coil may allow a device external to the patient within whom the device 2 is implanted to wirelessly transfer energy, through tissue of the patient, to recharge power source 4. Examples of power source 4 include, but are not limited to, lead acid batteries, nickel cadmium (NiCad) batteries, nickel metal hydride (NiMH) batteries, lithium ion (Li-ion) batteries, and lithium ion polymer (Li-ion polymer) batteries.

Power source 4 may provide power to one, some, or all of the various components of device 2. Power source 4 discharges due to the power consumed by the various components of device 2. Due to the discharging, power source 4 may need to be recharged or replaced periodically to ensure that power source 4 does not fully drain. Aspects of this disclosure provide techniques to determine how much charge has been delivered by power source 4, how much charge is remaining on power source 4, or how much time is remaining before power source 4 fully drains. Based on the determination, device 2 may indicate to a user of device 2, or some other entity, how much charge has been delivered or is remaining, or how much time is remaining before power source 4 fully drains. In this manner, the user of device 2, or some other entity, can recharge or replace power source 4 at an appropriate time before power source 4 fully drains.

Coulomb counter 6 may indicate an estimate of the amount of charge dissipated or accumulated by power source 4. As described in more detail below, processor 10 may estimate the charge level of power source 4 from the measurement of coulomb counter 6. The charge level estimate derived from measurements by coulomb counter 6 may be based on the amount of charge that power source 4 has delivered or the amount of charge remaining on power source 4. The charge level may be represented in terms of milliamp-Hours (mA-Hr), or some other unit of charge. The charge level estimate derived from the measurements by coulomb counter 6 may also be represented in terms of a percentage of full capacity, e.g., 90% of full capacity, a fraction of full capacity, e.g., ¼ of full capacity, a decimal equivalent of the percentage or fraction, e.g., 0.75 of full capacity, or any other representations.

In some examples, the amount of mA-Hr, or some other unit of charge, that indicates full capacity of power source 4, at a given state of power source 4, may be programmed in processor 10. For example, processor 10 may be programmed to indicate that 100 mA-Hr represents that power source 4 is fully charged when power source 4 has not been cycled multiple instances. Processor 10 may receive the amount of charge dissipated by power source 4 as measured by coulomb counter 6. Processor 10 may subtract the amount of delivered charge measurement, received from coulomb counter 6, from the amount of charge that represents full charge of power source 4. Processor 10 may then divide the resulting value by the amount of charge that represents full charge of power source 4. As one example, processor 10 may receive from coulomb counter 6 the value of 20 mA-Hr. 20 mA-Hr may represent the amount of charge dissipated by power source 4 as estimated by coulomb counter 6. Processor 10 may then subtract 20 mA-Hr from 100 mA-Hr which is 80 mA-Hr. A value of 100 mA-Hr may be programmed in processor 10 and may represent the amount of charge on power source 4 when power source 4 is charged for a given state of power source 4. Processor 10 may then divide 80 mA-Hr by 100 mA-Hr, resulting in an estimation that power source 4 is at 80% of full capacity, e.g., the charge level estimate derived from the measurement by coulomb counter 6 indicates that power sourc4 is at 80% of full capacity.

Coulomb counter 6 may be initialized to zero. In some examples, for every unit of charge that is delivered by power source 4, coulomb counter 6 may increment a counter by one. Alternatively, for every unit of charge delivered by power source 4, coulomb counter 6 may decrement a counter by one. Aspects of this disclosure are described with coulomb counter 6 incrementing the counter for ease of illustration. However, aspects of this disclosure may also be applicable to coulomb counters that decrement the counter. Furthermore, during charging of power source 4, coulomb counter 6 may count each unit of charge delivered to power source 4.

In some examples, either where coulomb counter 6 increments or decrements the counter, the counting by coulomb counter 6 may be inexact due to inherent integration drift within coulomb counter 6. To determine the amount of charge delivered by power source 4, coulomb counter 6 may integrate the current outputted by power source 4 over time. Small errors in the measurement of the current may result in progressively larger integration errors in charge level estimate derived from the measurements by coulomb counter 6 and further compounded into greater errors in the total charge level. Coulomb counter 6 may calculate the present state of charge of power source 4 from the previously calculated charge and the presently measured current. Therefore, errors caused by the integration drift may be cumulative and increase at a rate roughly proportional to the time.

Furthermore, errors caused by integration drift of coulomb counter 6 may be especially cumulative in rechargeable batteries. As noted above, power source 4 may be one or more rechargeable batteries. Due to the discharge/recharge cycling of power source 4 and the lower capacities of rechargeable batteries compared to non-rechargeable batteries, the integration drift of coulomb counter 6 increases with each discharge/recharge cycle. The integration drift of coulomb counter 6 may increase to a point where the charge level estimate, of power source 4, derived from the measurement by coulomb counter 6 is too uncertain to accurately estimate the actual charge level, e.g., when the degree of uncertainty exceeds a margin of error.

Accordingly, the charge level of power source 4 derived from the measurement by coulomb counter 6 may be an estimate of the actual charge level. The error in the measurement of coulomb counter 6, e.g., as caused by the drift, may be quantified as an uncertainty value. For example, there may be a +/−10% uncertainty in the measurement of coulomb counter 6. Accordingly, there may be a +/−10% uncertainty in the charge level estimate derived from the measurement by coulomb counter 6. For example, processor 10 may determine that the charge level estimate of power source 4 derived from the measurement by coulomb counter 6 indicates that power source 4 is at 50% of full capacity. However, there may be a +/−10% uncertainty in the estimate. In this example, the actual charge level may be between 40% of full capacity and 60% of full capacity, i.e., 50−10 and 50+10.

The uncertainty value associated with the charge level estimate derived from coulomb counter 6 may increase over time. The increase in the uncertainty value of the measurements derived from coulomb counter 6 may be modeled, measured, or provided by the manufacturer of coulomb counter 6. The increase in the uncertainty value may be linear as a function of time, as one example. The increase in the uncertainty may not be linear in all examples and may not be a function of time.

Figure 2A:
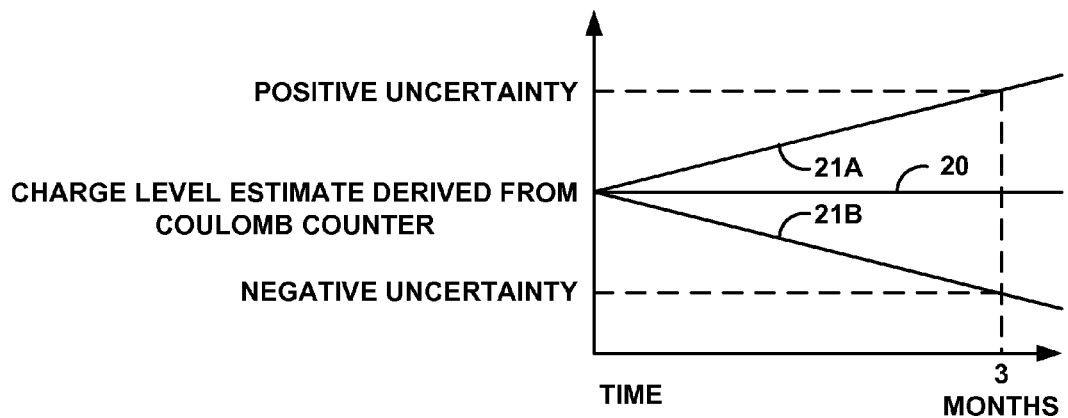
FIG. 2A is a graph illustrating an example of an increase in an uncertainty value for charge levels estimated using a coulomb counter over a period of time.

FIG. 2A is a graph illustrating an example of an increase in an uncertainty value for charge levels estimated using coulomb counter 6 over a period of time. In the example illustrated in FIG. 2A, line 20 represents the charge level estimate derived from the measurement by coulomb counter 6. As one example, after 3 months of operation, the charge level estimate derived from coulomb counter 6, by processor 10, may be 50 mA-Hr. Lines 21A, 21B illustrate the positive and negative uncertainty values, respectively, associated with the charge level estimate derived from the measurement by coulomb counter 6. As one example, after 3 months the uncertainty value associated with the charge level estimate derived from the measurement by coulomb counter 6 may be +/−5 mA-Hr. The uncertainty value, e.g., lines 21A, 21B, of the measurement by coulomb counter 6 may be considered as an error band, which may grow larger over time. The error band may define bounds for the actual charge level of power source 4. Accordingly, in the example illustrated in FIG. 2A, the actual charge level of power source 4 may be between 45 mA-Hr and 55 mA-Hr after 3 months of operation, i.e., 50−5 and 50+5. After three months, the error band grows larger in the example of FIG. 2A.

The manufacturer of coulomb counter 6, or some other entity, may model or measure the uncertainty values of coulomb counter 6 as a function of time. For example, the manufacturer of coulomb counter 6 may utilize the Monte-Carlo modeling technique, or a similar simulation technique, to model the uncertainty values of coulomb counter 6. The Monte-Carlo modeling technique may model the behavior of coulomb counter 6 based on the tolerances of coulomb counter 6 and the behavior of coulomb counter 6 over time.

As another example, rather than modeling the uncertainty of coulomb counter 6, the manufacturer of coulomb counter 6, or some other entity, may explicitly measure the uncertainty of coulomb counter 6 as a function of time. For example, a technician may couple a power source, such as power source 4, to a coulomb counter, such as coulomb counter 6, and a resistor with a known resistor value. The power source may be a new power source, e.g., fully charged without ever being discharged. In this example, the amount of charge provided by the power source may be calculated independently from the coulomb counter. For example, the technician may divide the voltage of the power source by the known resistor value to calculate the current through the resistor. The technician may then integrate the current over time to calculate the amount of charge provided by the power source. The technician may then compare the calculated amount of charge provided by the power source with the amount of charge counted by the coulomb counter. Any difference in the amount of charge provided by the power source as calculated and as determined by the coulomb counter may indicate the uncertainty value of that coulomb counter.

The technician may perform such calculations over time to determine the uncertainty values of the coulomb counter, such as coulomb counter 6, as a function of time. The technician may repeat these procedures for multiple different coulomb counters.

It should be noted that the previous example to determine the uncertainty in the amount of charge counted by coulomb counter 6 is merely provided for illustration purposes. Aspects of this disclosure should not be considered limited to the example provided to determine the uncertainty values of coulomb counter 6. There may be other techniques to determine the uncertainty in the amount of charge counted by coulomb counter 6.

It should also be noted that the example shown in FIG. 2A is provided for illustration purposes only. The uncertainty values as a function of time may be different for types of coulomb counters. Also, in examples where the manufacturer of coulomb counter 6 utilizes modeling techniques, the manufacturer of coulomb counter 6 may utilize modeling techniques other than the Monte-Carlo technique. The example illustration of FIG. 2A should not be considered as limiting.

Furthermore, although the uncertainty values are described in mA-Hr in the above example, aspects of this disclosure are not so limited. In some examples, the uncertainty value may be provided in terms of percentages, or other units pertinent to the charge level estimate. Aspects of this disclosure are described in terms of the uncertainty value being provided in terms of percentages. However, aspects of this disclosure are extendable to examples where the uncertainty value is provided in terms of mA-Hr, or other units pertinent to the charge level estimate. Processor 10 may convert the uncertainty values from mA-Hr to percentages, or vice-versa, by utilizing basic mathematical formulas. For instance, in the above example, the uncertainty is +/−5 mA-Hr, e.g., after three months the positive uncertainty value 21A may be 5 mA-Hr and negative uncertainty value 21B may be −5 mA-Hr. Also, as one example, processor 10 may be programmed to indicate that 100 mA-Hr represents the amount of charge on power source 4, for a given state of power source 4, when power source 4 is fully charged. In this example, +/−5 mA-Hr may represent +/−5%, i.e., +/−5 mA-Hr divided by 100 mA-Hr.

Referring back to FIG. 1, storage device 12 or a cache of processor 10 may store the uncertainty values of the measurements of coulomb counter 6 at different times in a look-up table. In some examples, in addition to or instead of storing the uncertainty values as a function of time, storage device 12 or the cache of processor 10 may store a formula for determining the uncertainty values as a function of time. Based on the formula, processor 10 may calculate the uncertainty values for a given time. As one example, the formula may be the slope of the uncertainty as shown in the example of FIG. 2A.

Timer 18 may provide the time to processor 10. In some examples, timer 18 may provide a clock from which processor 10 synchronizes its operation. In some examples, timer 18 may be initialized to zero and may start incrementing to indicate the amount of elapsed time. In some examples, timer 18 may also provide a timestamp for every time that processor 10 derived the charge level estimate from the measurement by coulomb counter 6. As described above, coulomb counter 6 may integrate the current delivered by power source 4 over time to determine an estimate of the amount of charge dissipated by power source 4. In some examples, coulomb counter 6 may not utilize the time provided by timer 18 to perform the integration. Rather, coulomb counter 6 may utilize its own internal timing mechanism to perform the integration. In some alternate examples, coulomb counter 6 may utilize the time provided by timer 18 to perform integration; however, aspects of the disclosure should be not considered limited as such.

Examples of processor 10 include, but are not limited to, a digital signal processor (DSP), general purpose microprocessor, application specific integrated circuit (ASIC), field programmable logic array (FPGA), or other equivalent integrated or discrete logic circuitry. Storage device 12 may comprise a computer-readable storage media. Examples of storage device 12 include, but are not limited to, random access memory (RAM), read only memory (ROM), electrically erasable programmable read-only memory (EEPROM), CD-ROM or other optical disk storage, magnetic disk storage, or other magnetic storage devices, flash memory, or any other medium that can be used to carry or store desired program code in the form of instructions or data structures and that can be accessed by a computer or a processor. In some aspects, storage device 12 may include instructions that cause processor 10 to perform the functions ascribed to processor 10 in this disclosure.

As described above, processor 10 may receive the amount of charge accumulated and/or depleted by power source 4 as measured by coulomb counter 6. Also, as described above, processor 10 may derive a charge level estimate, of power source 4, based on the measurement by coulomb counter 6. However, there may be an uncertainty value associated with the charge level estimate derived from the measurement by coulomb counter 6 due to the integration drift of coulomb counter 6. Due to the uncertainty in the charge level estimate derived from the measurement by coulomb counter 6, in some aspects of this disclosure, processor 10 may adjust the charge level estimate derived from the measurement by coulomb counter 6. In some examples, processor 10 may adjust the charge level estimate derived from the measurement by coulomb counter 6 based on the charge level estimate derived from another sensor.

In some examples, processor 10 may adjust the charge level estimate based on a charge level estimate derived from a voltage measurement, temperature measurement, impedance measurement, and/or size measurement of power source 4. Processor 10 may compare the uncertainty value associated with the charge level estimate derived from the measurement by coulomb counter 6 with the uncertainty value associated with the charge level estimate derived from the measured voltage, temperature, impedance, and/or size of power source 4. In some examples, based on the comparison, processor 10 may adjust the charge level estimate derived from the measurement by coulomb counter 6.

Power source meter 8 may be a meter to measure one or more characteristics of power source 4. The characteristics of power source 4 may include the voltage, pressure, temperature, impedance, and/or size of power source 4. Power source meter 8 provides the measured characteristic to processor 10. In some examples, power source meter 8 provides its measurements to A/D converter 14. A/D converter 14 converts the measurement to a digital value and provides the digital value to processor 10. Based on the measurement by power source meter 8, processor 10 may determine an estimation of the charge level of power source 4.

In some examples, the manufacturer of power source 4, or some other entity, may model the relationship of the charge level of power source 4 as a function of the measured characteristic of power source 4, e.g., voltage, pressure, temperature, impedance, and/or size of power source 4. For example, the manufacturer of power source 4, or some other entity using power source 4, may utilize Monte-Carlo modeling techniques to model the relationship between of the charge level and the measured characteristics of power source 4. The model of the relationship between the charge level and the measured characteristics of power source 4 may be stored in the internal cache of processor 10 or storage device 12 as a look-up table. In some examples, formulas that define the model may be stored in the cache of processor 10 or storage device 12. Processor 10 may determine the charge level of power source 4, based on the measured characteristics by power source meter 8, by utilizing the stored model of the relationship between the charge level and the measured characteristics of power source 4.

In some examples, rather than utilizing modeling techniques, the manufacturer of power source 4, or some other entity, may measure the relationship of the charge level of power source 4 as a function of the measured characteristic of power source 4. For example, the technician may calculate the amount of charge provided by power source 4 by coupling power source 4 to a resistor with a known value. The technician may measure the characteristic of power source 4, e.g., voltage, pressure, temperature, impedance, and/or size. The technician may associate the calculated amount of charge with the measured characteristic to determine the relationship between the charge level and the measured characteristics of power source 4.

It should be noted that the previous example to determine the charge level as a function of the measured characteristics is merely provided for illustration purposes. Aspects of this disclosure should not be considered limited to the example provided to determine the charge level as a function of the measured characteristics. There may be other techniques to determine the charge level as a function of the measured characteristics.

Like the charge level derived from the measurement by coulomb counter 6, there may be an uncertainty associated with the charge level estimate derived from the measured characteristic of power source 4. The stored model of the relationship between the charge level and the measured characteristic of power source 4 may also include the uncertainty value associated with the charge level estimate derived from the measurement by power source meter 8. As one example, where power source meter 8 measures the voltage of power source 4, the uncertainty value associated with the charge level estimate derived from the measured voltage of power source 4 may be caused by a flat battery voltage discharge of power source 4 and an inexactness in the measurement of the voltage of power source 4.

Figure 2B:
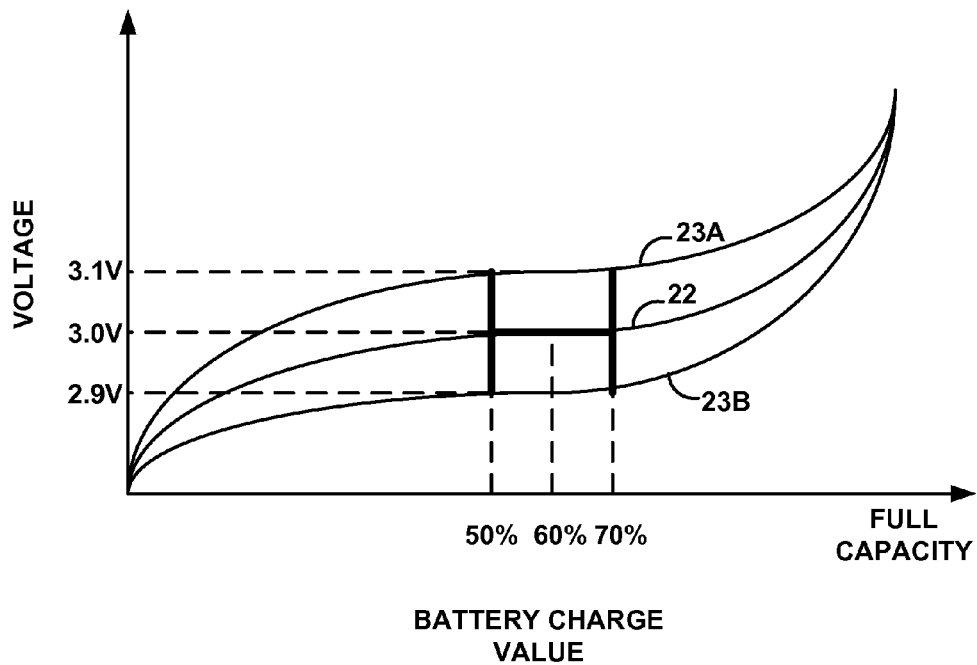
FIG. 2B is a graph illustrating an example of a relationship between charge level of a power source and a voltage of the power source.

FIG. 2B is a graph illustrating an example of a relationship between charge level and a voltage of power source 4. FIG. 2B also illustrates an example of the uncertainty values of the charge level derived from the measurement of the voltage of power source 4. It should be noted that like FIG. 2A, FIG. 2B is shown for illustration purposes only. The example illustrated in FIG. 2B should not be considered as limiting.

In the example illustrated in FIG. 2B, center line 22 represents the estimated charge level based on the measured voltage of power source 4. Upper line 23A and lower line 23B represent uncertainty values in the estimate, and the range of charge levels that could be expected. As power source 4 discharges, the voltage on power source 4 decreases. In some examples, due to the generally flat discharge curve of power source 4, at a certain point, the voltage of power source 4 may remain essentially constant even while discharging. For example, as illustrated in FIG. 2B, the voltage of power source 4 is 3.0V when the charge level is anywhere between 70% of full capacity and 50% of full capacity. As one example, the model of the relationship between the voltage of power source 4 and the charge level estimate may indicate that, when power source 4 is at approximately 3.0V, the charge level estimate is 60% of full capacity with uncertainty values of +/−10%, as illustrated in FIG. 2B.

There may be other causes for the uncertainty, in addition to the flat discharge characteristic of power source 4, in the charge level estimate derived from the measured voltage. The uncertainty in the charge level estimate derived from the measured voltage may be caused by changes in the behavior of power source 4 over time. For example, the behavior of power source 4 may change after multiple charge/discharge cycles. The uncertainty in the charge level estimate derived from the measure voltage may be cause by unit-to-unit variance of power source 4. For example, a first example of power source 4 may comprise a certain discharge curve, and a second example of power source 4 may comprise a different discharge curve.

Furthermore, the voltage measurement from power source meter 8 may not be exact. There may an uncertainty associated with the voltage measured by power source meter 8. For example, power source meter 8 may measure the voltage of power source 4 as being 3.0V when the actual voltage of power source 4 is 3.05V. Also, the precision of A/D converter 14 may not be exact. For example, there may be an uncertainty associated with the least significant bit (LSB) of the digital value generated by A/D converter 14. As one example, power source meter 8 may measure the voltage of power source 4 as 3.0V and, due to the uncertainty associated with A/D converter 14, the digital value generated by A/D converter 14 may indicate that the measured voltage is 3.1V or 2.9V.

It should be noted that charge level estimates derived from measurements by coulomb counter 6 and voltage measurements by power source meter 8 are provided for illustration purposes. In some examples, the manufacturer of power source 4, or some other entity, may model the charge level of power source 4 as a function of the pressure, temperature, impedance, or size of power source 4. For example, the manufacturer of power source 4, or some other entity, may generate models power source 4 that indicate the uncertainty of the charge level estimate based on the charge level estimate as a function of pressure, temperature, impedance, or size of power source 4. The model, or formulas that represent the model, may be stored in the internal cache of processor 10 or storage device 12.

In some instances, the pressure, temperature, impedance, or size of power source 4 may change as power source 4 discharges or charges. For example, as power source 4 discharges, power source 4 may swell, e.g., the size of power source 4 may change. As another example, as power source 4 discharges or charges, the pressure, temperature, and impedance of power source 4 may change. Accordingly, power source meter 8 may be configured to measure one or more of the voltage, pressure, temperature, impedance, and size of power source 4, as a few non-limiting examples.

Referring back to FIG. 1, as described above, processor 10 may receive the charge level estimate derived from the measurement by coulomb counter 6. Processor 10 may also receive or calculate the uncertainty value associated with the charge level estimate derived from the measurement by coulomb counter 6 based on the amount of elapsed time indicated by timer 18. Processor 10 may also receive the digital value from A/D converter 14 that represents the measurement by power source meter 8 of power source 4, e.g., the voltage measurement of power source 4. Processor 10 may then determine the charge level estimate based on the measurement by power source meter 8. As described above, the model of the relationship between the charge level and the measurement by power source meter 8 of power source 4 may be stored in the internal cache of processor 10 or storage device 12 as a look-up table. In some examples, formulas that define the model may be stored in the cache of processor 10 or storage device 12. Processor 10 may utilize the stored model of the relationship between the measurement by power source meter 8 and the charge level to determine an estimation of the charge level. Processor 10 may also receive or calculate the uncertainty value associated with the charge level estimate derived from the measurement by power source meter 8 based on the stored model.

It should be noted that coulomb counter 6 is provided for illustration purposes, and should not be considered as limiting. In examples of device 2 that do not include coulomb counter 6, timer 18 may also not be needed. In such examples, power source meter 8 may measure at least two characteristics of power source 4. For example, power source meter 8 may measure the voltage of power source 4 and the pressure of power source 4. Processor 10 may determine the charge level estimate derived from the measured voltage and the measured pressure, as well as, uncertainty values of the charge level estimates derived from the measured voltage and measured pressure. Processor 10 may similarly determine charge level estimates derived from impedance and size measurements of power source 4.

In general, processor 10 may determine charge level estimates derived from at least two measurements of power source 4, and corresponding uncertainty values for each measurement. For example, processor 10 may determine charge level estimates derived from coulomb counter 6 and the pressure measurement of power source 4, and uncertainty values for the charge level estimate derived from the measurement by coulomb counter 6 and the pressure measurement by power source meter 8. As another example, processor 10 may determine charge level estimates derived from the pressure, temperature, and impedance measurements of power source 4, and uncertainty values for the charge level estimate derived from the pressure, temperature, and impedance measurements by power source meter 8. In general, processor 10 may derive charge level estimates, and uncertainty values of the estimates, from combination of measurements by coulomb counter 6 and the measurements by power source 4 of one or more of the voltage, pressure, temperature, impedance, and/or size of power source 4.

Not every measurement, of the above non-limiting example measurements, may be necessary in every instance of this disclosure. For purposes of illustration and clarity, some aspects of this disclosure are described in the context of processor 10 determining charge level estimates derived from measurements by coulomb counter 6 and voltage measurements by power source meter 8. Also, for purposes of illustration and clarity, aspects of this disclosure are described in the context of processor 10 determining uncertainty values associated with the charge level estimates derived from measurements by coulomb counter 6 and voltage measurements by power source meter 8. However, aspects of this disclosure should not be considered limited as such.

In some aspects, processor 10 may compare the uncertainty value associated with charge level estimates derived from at least two different techniques to estimate charge level. For example, processor 10 may compare the uncertainty value associated with the charge level estimate derived from the measurement by coulomb counter 6 with the uncertainty value associated with the charge level estimate derived from the measured voltage of power source 4. Based on the comparison, processor 10 may adjust the charge level estimate derived from at least one of the charge level estimate measurement techniques. For example, processor 10 may adjust the charge level estimate derived from the measurement by coulomb counter 6 based on the charge level estimate derived from the voltage measurement of power source 4. The adjusted charge level estimate may be referred to as a bounded charge level estimate because the adjusted charge level estimate is bounded by the uncertainty value associated with the adjusted charge level estimate.

As one example, if the uncertainty value associated with the charge level derived from the measured voltage is less than the uncertainty value associated with charge level estimate derived from the measurement by coulomb counter 6, processor 10 may adjust the charge level estimate derived from the measurement by coulomb counter 6 to be substantially equal to the charge level estimate derived from the measured voltage of power source 4. In this manner, the uncertainty of the adjusted charge level estimate can be minimized to the uncertainty value of the charge level estimate derived from the measurement of the voltage of power source 4.

Figure 3A:
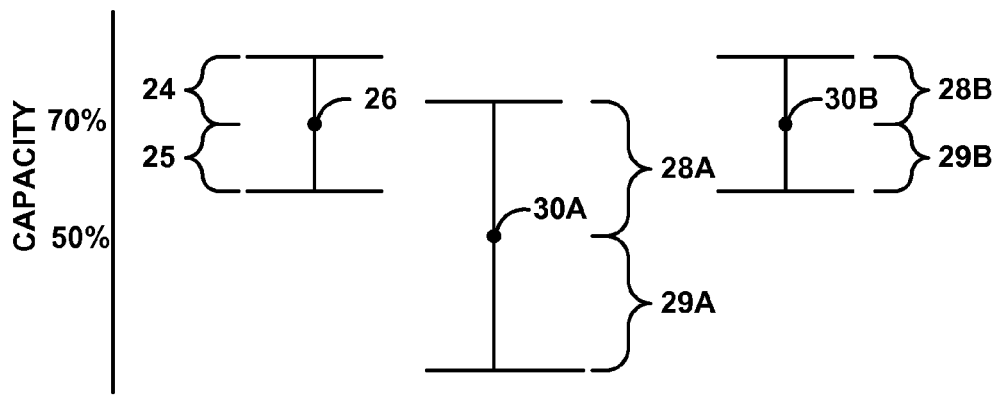
FIG. 3A is a diagram illustrating an example of a process for adjusting the charge level estimate derived from a measurement by a coulomb counter based on the uncertainty value of the charge level estimate derived from the voltage measurement of a power source and the uncertainty value of the charge level estimate derived from a measurement by a coulomb counter.

FIG. 3A is a diagram illustrating an example of a process for adjusting the charge level estimate derived from the measurement by coulomb counter 6 based on the uncertainty value of the charge level estimate derived from the voltage measurement of power source 4 and the uncertainty value of the charge level estimate derived from the measurement by coulomb counter 6. The example illustrated in FIG. 3A may be applicable when the uncertainty value of the charge level estimate derived from the voltage measurement is less than the uncertainty value of the charge level estimate derived from the measurement by coulomb counter 6.

In the example illustrated in FIG. 3A, charge level estimate 26 is derived from the measured voltage of power source 4. Charge level estimate 26 indicates that power source 4 is at 70% of full capacity, in the illustrated example. Uncertainty values 24 and 25 are the plus and minus uncertainty values associated with charge level estimate 26. Accordingly, the actual charge level, of power source 4, may be between charge level estimate 26 plus uncertainty 24 and charge level estimate 26 minus uncertainty 25.

Charge level estimate 30A is the charge level estimate derived from the measurement by coulomb counter 6. Charge level estimate 30A indicates that power source 4 is at 50% of full capacity, in the illustrated example of FIG. 3A. Uncertainty values 28A and 29A are the plus and minus uncertainty values associated with charge level estimate 30A. Accordingly, the actual charge level may be between charge level estimate 30A plus uncertainty 28A and charge level 30A minus uncertainty 29A.

As shown in FIG. 3A, the combined uncertainty of uncertainty values 28A and 29A is greater than the combined uncertainty of uncertainty values 24 and 25. In some of these instances, processor 10 may adjust the charge level estimate derived from the measurement by coulomb counter 6, e.g., charge level estimate 30A. Processor 10 may adjust charge level estimate 30A such that charge level estimate 30A is substantially the same as the charge level estimate derived from the measured voltage of power source 4, e.g., charge level estimate 26. Processor 10 may choose charge level estimate 26 because the combined uncertainty values associated with charge level estimate 26, e.g., uncertainty values 24 and 25, is less than the combined uncertainty values associated with charge level estimate 30A, e.g., uncertainty values 28A and 29A.

Charge level estimate 30B indicates the adjusted charge level estimate 30A. Charge level estimate 30B may be referred to as a bounded charge level estimate. As shown in FIG. 3A, charge level estimate 30B is substantially the same as charge level estimate 26. Uncertainty values 28B and 29B are the plus and minus uncertainty values of charge level estimate 30B. Uncertainty vales 28B and 29B are substantially the same as uncertainty values 24 and 25, which is less than uncertainty values 28A and 29A. Accordingly, after adjustment, the adjusted charge level estimate may be a better approximation of the actual charge level and the uncertainty of the charge level estimate may be reduced.

Referring back to FIG. 1, in some instances, the uncertainty value of the charge level estimate derived from the voltage measurement of power source 4 may be greater than the uncertainty value of the charge level estimate derived from the measurement by coulomb counter 6. In some of these instances, processor 10 may determine whether the maximum charge level estimate derived from the measurement by coulomb counter 6 is greater than the maximum charge level estimate derived from the voltage measurement of power source 4. For example, the charge level estimate derived from the measurement by coulomb counter 6 may indicate that the charge level estimate is 60% of full capacity with an uncertainty value of +/−10%. The charge level estimate derived from the voltage measurement may indicate that the charge level estimate is 45% of full capacity with an uncertainty value of +/−20%. In this example, the maximum charge level estimate derived from the measurement of coulomb counter 6 is 70% of full capacity, i.e., 60+10. The maximum charge level estimate derived from the voltage measurement is 65% of full capacity, i.e., 45+20.

If the maximum charge level estimate derived from the measurement of coulomb counter 6 is greater than the maximum charge level estimate derived from the voltage measurement, processor 10 may adjust the charge level estimate derived from the measurement by coulomb counter 6. In some of these instances, processor 10 may adjust the charge level estimate derived from the measurement by coulomb counter 6 such that the maximum adjusted charge level estimate is substantially equal to the maximum charge level estimate derived from the voltage measurement. In this manner, the uncertainty of the adjusted charge level estimate is minimized, and the adjusted charge level estimate is kept within the minimized uncertainty.

Figure 3B:
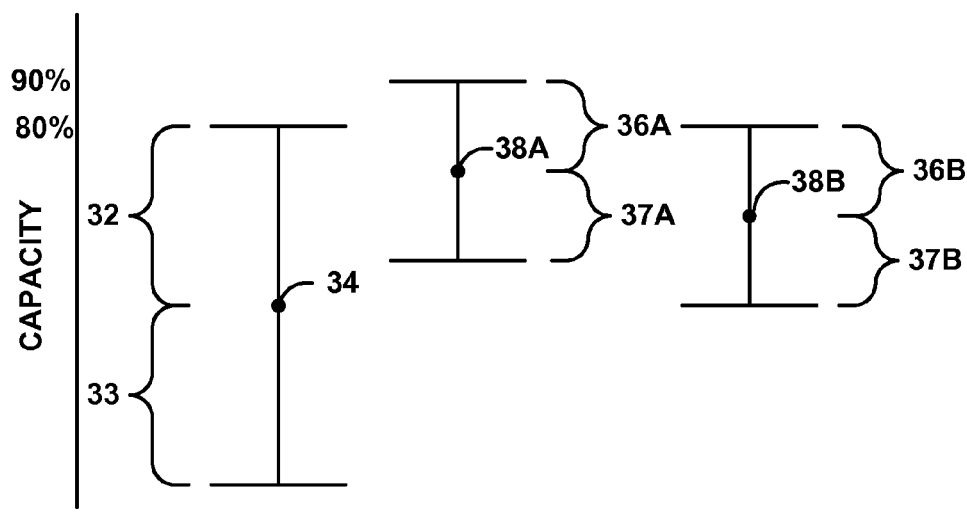
FIG. 3B is a diagram illustrating another example of a process for adjusting the charge level estimate derived from a measurement by a coulomb counter based on the uncertainty value of the charge level estimate derived from the voltage measurement of a power source and the uncertainty value of the charge level estimate derived from a measurement by a coulomb counter.

FIG. 3B is a diagram illustrating another example of a process for adjusting the charge level estimate derived from the measurement by coulomb counter 6 based on the uncertainty value of the charge level estimate derived from the voltage measurement of power source 4 and the uncertainty value of the charge level estimate derived from the measurement by coulomb counter 6. The example illustrated in FIG. 3B may be applicable when the uncertainty value of the charge level estimate derived from the voltage measurement is greater than the uncertainty value of the charge level estimate derived from the measurement by coulomb counter 6.

Charge level estimate 34 is the charge level estimate derived from the voltage measurement of power source 4. Uncertainty values 32 and 33 are the plus and minus uncertainty values of charge level estimate 34. Charge level estimate 38A is the charge level estimate derived from the measurement by coulomb counter 6. Uncertainty values 36A and 37A are the plus and minus uncertainty values of charge level estimate 38A. In the example illustrated in FIG. 3B, the combined uncertainty of uncertainty values 32 and 33 is greater than the combined uncertainty of uncertainty values 36A and 37A.

As shown in FIG. 3B, the maximum charge level estimate derived from the voltage measurement is 80% of full capacity, e.g., charge level estimate 34 plus uncertainty 32. The maximum charge level estimate derived from the measurement by coulomb counter 6 is 90% of full capacity, e.g., charge level estimate 38A plus uncertainty 36A. Because the maximum charge level estimate derived from the measurement by coulomb counter 6 is greater than the maximum charge level estimate derived from the voltage measurement, processor 10 may adjust charge level estimate 38A. Processor 10 may adjust charge level estimate 38A such that the maximum charge level estimate of the adjusted charge level estimate is substantially the same as the maximum charge level estimate derived from the measured voltage of power source 4.

In the example illustrated in FIG. 3B, charge level estimate 38B indicates the adjusted charge level estimate 38A. Charge level estimate 38B may be referred to as a bounded charge level estimate. Uncertainty values 36B and 37B are the plus and minus uncertainty values of charge level estimate 38B. Uncertainty values 36B and 37B may be substantially the same as uncertainty values 36A and 37A.

To adjust the charge level estimate derived from the measurement by coulomb counter 6, processor 10 may subtract the uncertainty value of the charge level estimate derived from the measurement by coulomb counter 6 from the maximum charge level estimate derived from the voltage measurement of power source 4, in examples where the uncertainty value is provided in +/− percentage. In the example illustrated in FIG. 3B, assume uncertainty values 36A and 37A are each 20%. To calculate charge level estimate 38B, processor 10 may subtract 20 from 80, which results in 60% of full capacity.

Referring back to FIG. 1, the uncertainty value for the charge level estimate derived from the voltage measurement of power source 4 may be greater than the uncertainty value of the charge level estimate derived from the measurement by coulomb counter 6. However, the maximum charge level estimate derived from the measurement by coulomb counter 6 may not be greater than the maximum charge level estimate derived from the voltage measurement of power source 4. In some these instances, processor 10 may determine whether the minimum charge level estimate derived from the measurement by coulomb counter 6 is less than the minimum charge level estimate derived from the voltage measurement of power source 4.

For example, the charge level estimate derived from the measurement by coulomb counter 6 may indicate that the charge level estimate is 60% of full capacity with an uncertainty value of +/−10%. The charge level estimate derived from the voltage measurement may indicate that the charge level estimate is 70% of full capacity with an uncertainty value of +/−15%. In this example, the minimum charge level estimate derived from the measurement by coulomb counter 6 is 50% of full capacity, i.e., 60−10. The minimum charge level estimate derived from the voltage measurement is 55% of full capacity, i.e., 70−15.

If the minimum charge level estimate derived from the measurement by coulomb counter 6 is less than the minimum charge level estimate derived from the voltage measurement, processor 10 may adjust the charge level estimate derived from the measurement by coulomb counter 6. In some of these instances, processor 10 may adjust the charge level estimate derived from the measurement by coulomb counter 6 such that the minimum adjusted charge level estimate is substantially equal to the minimum charge level estimate derived from the voltage measurement.

Figure 3C:
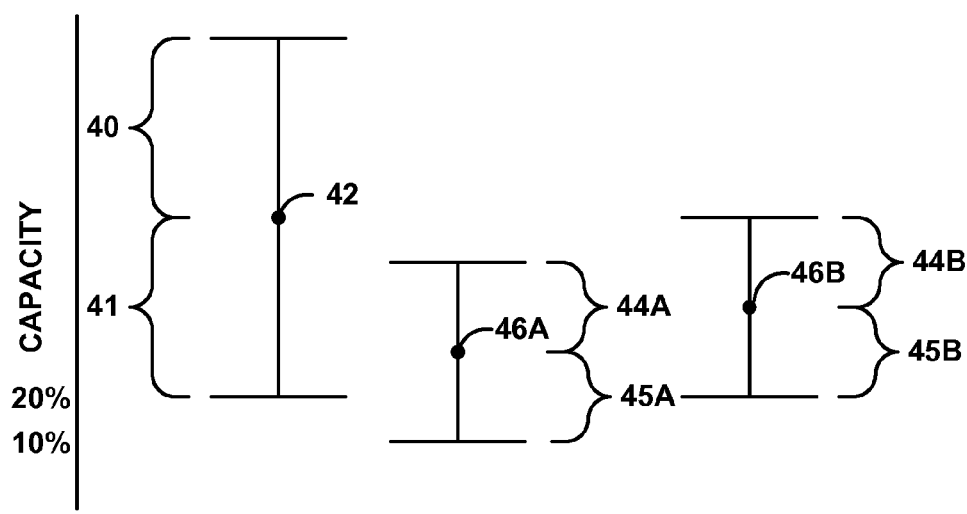
FIG. 3C is a diagram illustrating another example of a process for adjusting the charge level estimate derived from a measurement by a coulomb counter based on the uncertainty value of the charge level estimate derived from the voltage measurement of a power source and the uncertainty value of the charge level estimate derived from a measurement by a coulomb counter.

FIG. 3C is a diagram illustrating another example of a process for adjusting the charge level estimate derived from the measurement by coulomb counter 6 based on the uncertainty value of the charge level estimate derived from the voltage measurement of power source 4 and the uncertainty value of the charge level estimate derived from the measurement by coulomb counter 6. The example illustrated in FIG. 3C may be applicable when the uncertainty value of the charge level estimate derived from the voltage measurement is greater than the uncertainty value of the charge level estimate derived from the measurement by coulomb counter 6.

Charge level estimate 42 is the charge level estimate derived from the voltage measurement of power source 4. Uncertainty values 40 and 41 are the plus and minus uncertainty values of charge level estimate 42. Charge level estimate 46A is the charge level estimate derived from the measurement by coulomb counter 6. Uncertainty values 44A and 45A are the plus and minus uncertainty values of charge level estimate 46A. In the example illustrated in FIG. 3C, the combined uncertainty of uncertainty values 40 and 41 is greater than the combined uncertainty of uncertainty values 44A and 45A.

As shown in FIG. 3C, the minimum charge level estimate derived from the voltage measurement is 20% of full capacity, e.g., charge level estimate 42 minus uncertainty 41. The minimum charge level derived from the measurement by coulomb counter 6 is 10% of full capacity, e.g., charge level estimate 46A minus uncertainty 45A. Because the minimum charge level estimate derived from the measurement by coulomb counter 6 is less than the minimum charge level estimate derived from the voltage measurement, processor 10 may adjust charge level estimate 46A. Processor 10 may adjust charge level estimate 46A such that the minimum charge level estimate of the adjusted charge level estimate is substantially the same as the minimum charge level estimate derived from the measured voltage of power source 4.

In the example illustrated in FIG. 3C, charge level estimate 46B indicates the adjusted charge level estimate 46A. Charge level estimate 46B may be referred to as a bounded charge level estimate. Uncertainty values 44B and 45B are the plus and minus uncertainty values of charge level estimate 46B. Uncertainty values 44B and 45B may be substantially the same as uncertainty values 44A and 45A.

To adjust the charge level estimate derived from the measurement by coulomb counter 6, processor 10 may sum the minimum charge level estimate derived from the measured voltage with the uncertainty value associated with the charge level estimate derived from the measurement by coulomb counter 6, in examples where the uncertainty is provided in +/− percentage. In the example illustrated in FIG. 3C, assume uncertainty 44A and 45A are each 30%. To calculate charge level estimate 46B, processor 10 may sum 20% and 30%, which results in 50% of full capacity.

As described above, in the examples illustrated in FIGS. 3A, 3B, and 3C, processor 10 may adjust the charge level estimate derived from the measurement by coulomb counter 6 based on the charge level estimate derived from the voltage measurement of power source 4. However, aspects of this disclosure are not so limited. In some examples, processor 10 may adjust the charge level estimate derived from the voltage measurement based on the charge level estimate derived from the measurement by coulomb counter 6 in substantially similar manners as those described above with respect to FIGS. 3A, 3B, and 3C.

Moreover, in some examples, the two charge level estimates need not be derived from the measurement by coulomb counter 6 and the voltage measurement of power source 4. In some examples, processor 10 may adjust the charge level estimate derived from any technique to estimate charge level based on a charge level estimate derived from one or more other techniques to estimate the charge level. As described above, techniques to derive an estimate of the charge level include, but are not limited to, measurements by coulomb counter 6, as well as, measurements by power source meter 8 including voltage measurements, pressure measurements, impedance measurements, and size measurements.

Furthermore, as described above, processor 10 may adjust a charge level estimate based on another charge level estimate and the uncertainty values associated with the two charge level estimates. However, in some examples, processor 10 may adjust a charge level estimate based on more than one other charge level estimate. For example, processor 10 may adjust a charge level estimate derived from the measurement by coulomb counter 6 based on the charge level estimate derived from a pressure and temperature measurement of power source 4, as well as, the uncertainty value associated with the charge level estimate derived from the measurement by coulomb counter 6, the uncertainty value associated with the charge level estimate derived from the pressure measurement, and the uncertainty value associated with the charge level estimate derived from the temperature measurement. Other possible permutations and combinations may be possible, and are contemplated by this disclosure.

In some examples, after processor 10 adjusts the charge level estimate, processor 10 may provide the adjusted charge level estimate to a user of device 2. In some examples, such as when device 2 is an IMD, processor 10 may provide the adjusted charge level estimate to telemetry module 16 (FIG. 1). Telemetry module 16 may comprise circuitry for wired or wireless communication between device 2 and another device or network. Telemetry module 16 may include filters, modulators, de-modulators and the like to effectuate wired or wireless communication.

After receiving the adjusted charge level estimate, telemetry module 16 may transmit the adjusted charge level estimate to another device. In examples where device 2 is an IMD, telemetry module 16 may wirelessly transmit the adjusted charge level estimate to an external programmer. The external programmer may then display the charge level estimate to the patient, a physician, and/or technician. For example, the external programmer may indicate that the power source 4 is at 50% of full capacity.

As another example, processor 10 may estimate the amount of time remaining before power source 4 fully drains based on the adjusted charge level estimate. Timer 18 may indicate the amount of time that elapsed when the charge level of power source 4 is approximately the adjusted charge level estimate. Based on the amount of elapsed time indicated by timer 18, processor 10 may estimate the amount of time remaining before power source 4 fully drains given the adjusted charge level estimate. For example, timer 18 may indicate that the elapsed time is one year and processor 10 may determine that the adjusted charge level estimate indicates that power source 4 is approximately 50% of full capacity. In this example, processor 10 may determine that power source 4 may fully drain after another year. Processor 10 may provide an estimation of the amount of time remaining, e.g., in units of hours, minutes, or seconds, before power source 4 fully drains.

In some examples, processor 10 may also provide the uncertainty value associated with the adjusted charge level estimate for presentation. In this manner, the user of device 2 may be informed of the uncertainty of the displayed charge level estimate. For example, the patient, within whom device 2 is implanted, a physician, a technician, or other caregiver may be informed of the uncertainty of the displayed charge level estimate. The uncertainty value may provide the patient, physician, technician, or caregiver with additional information about when and whether to replace or recharge power source 4. The uncertainty value may be considered as measurement of confidence, e.g., a figure of merit, of the charge level estimate. The figure of merit may indicate the confidence of the charge level estimate determined by processor 10.

For example, the external programmer may receive, from device 2 via telemetry module 16, the adjusted charge level estimate, which may indicate that the charge level estimate is 30% of full capacity with an uncertainty of +/−5%. The external programmer may display the charge level estimate and the uncertainty value. Based on the charge level estimate, the patient may determine that it is appropriate to recharge or replace power source 4. As another example, the external programmer may receive, from device 2 via telemetry module 16, the amount of time remaining before power source 4 drains, which may be a 100 days with an uncertainty of 12 hours. The external programmer may display the charge level estimate and the uncertainty value, and the patient may decide to wait a few days before replacing or recharging power source 4. In some examples, as described in more detail below, rather than device 2 providing the charge level estimate and uncertainty value, the external programmer may perform the computations to determine the charge level estimate and uncertainty value.

In some examples, rather than providing the adjusted charge level estimate for display, processor 10 may provide the adjusted charge level estimate minus the uncertainty value of the adjusted charge level estimate. For example, referring to FIG. 3A, in some examples, rather the providing adjusted charge level estimate 30B, in some examples, processor 10 may subtract uncertainty value 29B from adjusted charge level estimate 30B. Processor 10 may then provide the resulting charge level estimate to telemetry module 16 for subsequent presentation. In this manner, the patient, or some other entity, is provided with the minimum charge level estimate which may possibly further ensure that the patient, or some other entity, replaces or recharges power source 4 at appropriate times. Although the previous example is provided with respect to FIG. 3A, the minimum charge level estimate may be calculated similarly for the examples illustrated in FIGS. 3B and 3C.

Based on the presented charge level estimate, the user of device 2, e.g., the patient, physician, technician, or caregiver, may determine when it is optimal to recharge or replace power source 4. As described above, aspects of this disclosure may provide a better approximation of the actual charge level. Therefore, the user of device 2 may be in a better position to determine when and whether to recharge or replace power source 4 before power source 4 fully drains. Moreover, in examples where the user of device 2 is provided the minimum charge level estimate, the user may recharge or replace power source 4 more often. Accordingly, the user of device 2 may further ensure that power source 4 is recharged or replaced before power source 4 fully drains.

In some aspects of this disclosure, some of the components in device 2 may be preprogrammed to enter reduced power mode, e.g., sleep mode, when the charge level estimate of power source 4 is below a threshold, e.g., 5% of full capacity. Accordingly, by providing the user of device 2 with a better approximation of the charge level estimate, the user may be able to replace or recharge power source 4 before the components in device 2 enter the reduced power mode.

As described above, in some non-limiting examples, processor 10 derives the charge level estimate from the measurement by coulomb counter 6 and derives the charge level estimate from the voltage measurement of power source 4. Also, as described above, in some non-limiting examples, processor 10 determines the uncertainty values associated with the charge level estimate derived from the measurement by coulomb counter 6 and the charge level estimate derived from the measured voltage. Processor 10 may then adjust the charge level estimate derived from the measurement by coulomb counter 6. However, aspects of this disclosure are not so limited.

In some examples, some or all of the functionality ascribed to processor 10 may be performed by an external programmer or some other device. For instance, instead of or in addition to processor 10 adjusting the charge level estimate, a device other than device 2 may provide such functionality of processor 10. For example, processor 10 may transmit the measurement by coulomb counter 6 and the measured voltage of power source 4 via telemetry module 16 to the external programmer, or some other device. The external programmer or the other device may estimate the charge level based on the measurements. The external programmer or the other device may then determine the uncertainty values associated with the charge level estimates. For example, the external programmer or the other device may store the model of the uncertainty values of coulomb counter 6 as a function of time, and may also store the model of the charge level, of power source 4, as a function of the measured voltage. Based on the stored models, the external programmer or the other device may then calculate the uncertainty values associated with charge level estimated derived from the measurement by coulomb counter 6 and the charge level estimate derived from the measured voltage of power source 4 utilizing techniques similar to those described above.

Similarly, devices other than device 2 may determine the charge level estimates derived from any of the example techniques described above in a substantially similar manner. For example, devices other than device 2 may receive measurements of pressure, temperature, impedance, and/or size of power source 4. Based on such measurements, devices other than device 2 may estimate the charge level utilizing the techniques described above.

Accordingly, some of the functionality ascribed to device 2 in this disclosure may also be performed by the external programmer or some other device. For purposes of ease of illustration, aspects of this disclosure are described in the context of processor 10 performing the various functions to adjust the charge level estimate derived from at least one technique to estimate the charge level of power source 4. However, the external programmer or some other device may include a processor substantially similar to processor 10 that performs similar functions to those ascribed in this disclosure to processor 10.

In aspects of this disclosure, processor 10 may be associated with a medical device. For example, device 2 may be considered as a medical device that includes processor 10. In this example, processor 10 is associated with the medical device 2. As described above, the external programmer, or some other device, may also include a processor similar to processor 10 that performs functions similar to those described in this disclosure. The external programmer, or another device, may be considered as a medical device because they are used in conjunction with providing medical therapy. In these examples, the programmer or another device may be considered as a medical device.

Figure 4:
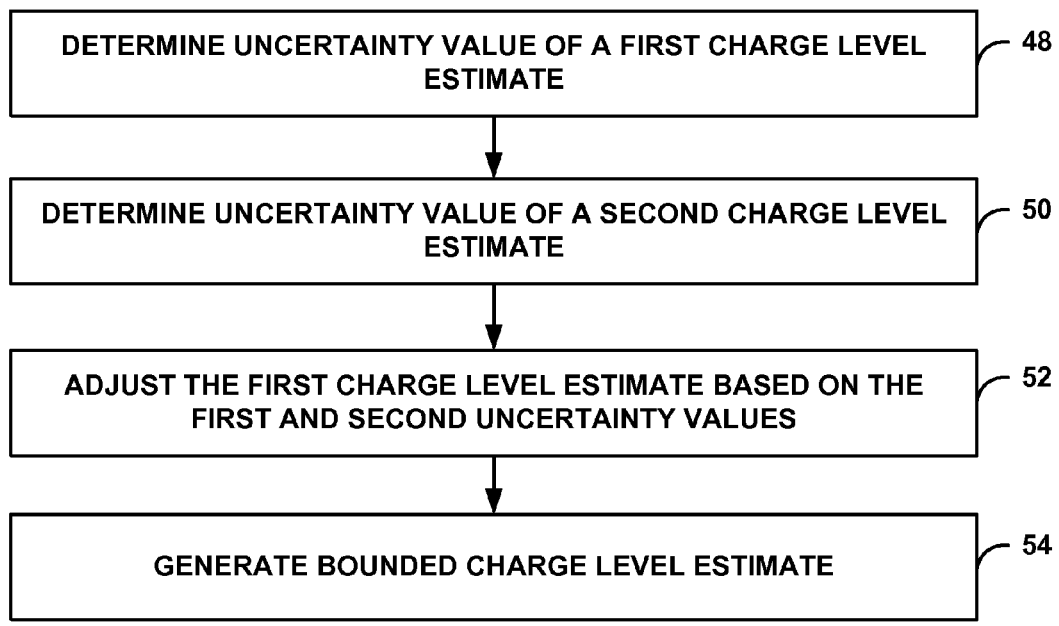
FIG. 4 is a flow chart illustrating example operation of a processor, or some other device, to estimate charge level of a power source in a device.

FIG. 4 is a flow chart illustrating an example operation of processor 10, or some other device, to estimate charge level of a power source in a device. For purposes of illustration, reference is made to FIG. 1. Processor 10 may determine an uncertainty value associated with a first charge level estimate of power source 4 (48). The first charge level estimate may be derived from the measurement by coulomb counter 6, a voltage measurement, a pressure measurement, a temperature measurement, an impedance measurement, or a size measurement of power source 4 measured by power source meter 8. To determine the uncertainty value associated with the first charge level estimate, in some examples, processor 10 may receive the uncertainty level from a cache of processor 10 or from storage device 12. In some examples, processor 10 may receive a formula of the uncertainty values as a function of time, processor 10 may then calculate the uncertainty values associated with the first charge level estimate based on the formula and the elapsed time provided by timer 18.

Processor 10 may determine an uncertainty value associated with a second charge level estimate (50). The second charge level estimate may be derived from a technique other than the technique to generate the first charge level estimate. The second charge level estimate indicates the charge level estimate of power source 4. In non-limiting examples, the second charge level estimate may be derived from the measurement by coulomb counter 6, a voltage measurement, a pressure measurement, a temperature measurement, an impedance measurement, or a size measurement of power source 4 measured by power source meter 8. Cache of processor 10 or storage device 12 may store charge level estimates as a function of the measurement of power source 4. In some examples, cache of processor 10 or storage device 12 may store information defining formulas from which processor 10 can calculate an estimate of the charge levels as a function of the measurement of power source 4.

In some examples, in addition to the storage of charge level estimates, cache of processor 10 or storage device 12 may include uncertainty values associated with the charge level estimates. Processor 10 may determine the uncertainty value associated with the second charge level estimate based on the stored uncertainty values.

Processor 10 may adjust the first charge level estimate based on the first and second uncertainty values (52). Processor 10 may then generate the bounded charge level estimate based on the adjustment (54).

Figure 5:
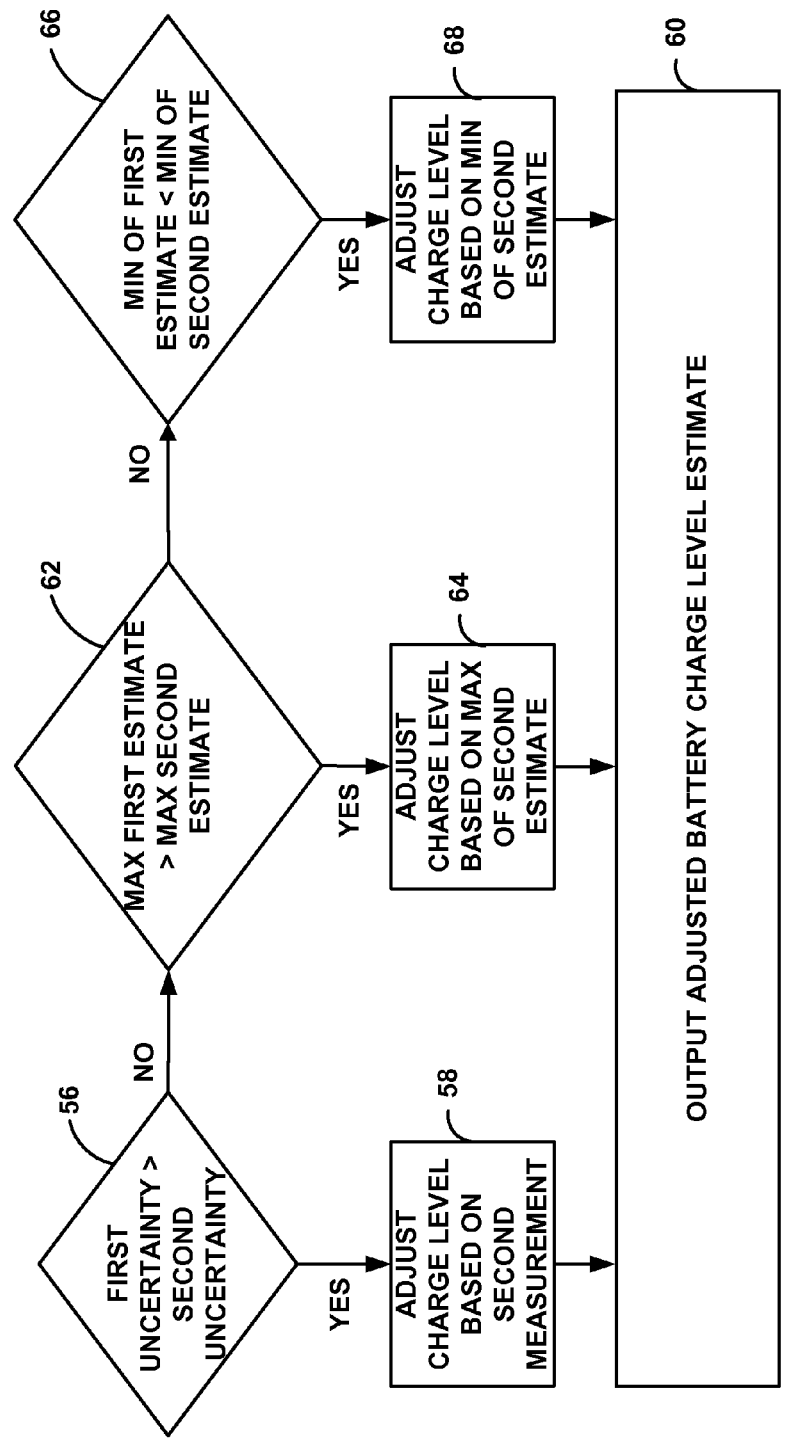
FIG. 5 is a flow chart illustrating an example of adjusting a charge level estimate based on a comparison of uncertainty values.

FIG. 5 is a flow chart illustrating an example of adjusting a charge level estimate based on a comparison of uncertainty values. For purposes of illustration, reference is made to FIG. 1. The acts described with respect to FIG. 5 may be preformed by processor 10, the external programmer, or some other device. For ease of illustration, FIG. 5 is described with respect to processor 10. Processor 10 may determine whether an uncertainty value associated with a first charge level estimate is greater than an uncertainty value associated with a second charge level estimate (56). In some examples, the first and second charge level estimates may be the charge level estimate derived by processor 10 from the measurement by coulomb counter 6, or the charge level estimate derived by processor 10 from the measurement of voltage, pressure, temperature, impedance, or size of power source 4 measured by power source meter 8. Processor 10 may calculate the uncertainty value of the first and second charge level estimates by utilizing the techniques described above.

If the uncertainty value of the first charge level estimate is greater than the uncertainty value of the second charge level estimate (YES of 56), processor 10 may adjust the first charge level estimate such that the adjusted first charge level estimate is substantially the same as the second charge level estimate (58). The adjusted charge level estimate may be referred to as a bounded charge level estimate. After adjustment, in some cases, processor 10 may output the adjusted charge level estimate via telemetry module 16 for presentation of the adjusted charge level estimate (60). However, it may not be necessary for processor 10 to output the adjusted charge level for presentation in every example.

If the uncertainty value of the first charge level estimate is less than the uncertainty value of the second charge level estimate (NO of 56), processor 10 may determine whether the maximum charge level estimate from the first charge estimate is greater than the maximum charge level estimate from the second charge estimate (62). To calculate the maximum charge level estimate from the first charge level estimate, processor 10 may sum the uncertainty value of the first charge level estimate with the first charge level estimate (assuming the uncertainty value is expressed as a percentage of the battery charge level). To calculate the maximum charge level estimate from the second charge level estimate, processor 10 may sum the uncertainty value of the second charge level estimate with the second charge level estimate (again, assuming the uncertainty value is expressed as a percentage of the battery charge level).

If the maximum charge level estimate from the first charge level estimate is greater than the maximum charge level estimate from the second charge level estimate (YES of 62), processor 10 may adjust the first charge level estimate based on the maximum charge level estimate from the second charge level estimate (64). To adjust the charge level estimate, processor 10 may subtract the uncertainty value of the first charge level estimate from the maximum charge level estimate from the second charge level estimate.

After adjustment, in some cases, processor 10 may output the adjusted charge level estimate via telemetry module 16 for presentation of the adjusted charge level estimate (60). Again, it may not be necessary for processor 10 to output the adjusted charge level estimate for presentation in every example.

If the maximum charge level estimate from the first charge level estimate is not greater than the maximum charge level estimate derived from the second charge level estimate (NO of 62), processor 10 may determine whether the minimum charge level estimate from the first charge level estimate is less than the minimum charge level estimate from the second charge level estimate (66). To calculate the minimum charge level estimate from the first charge level estimate, processor 10 may subtract the uncertainty value of the first charge level estimate from the first charge level estimate (assuming the uncertainty value is expressed as a percentage of the battery charge level). To calculate the minimum charge level estimate from the second charge level estimate, processor 10 may subtract the uncertainty value of the second charge level estimate from the second charge level estimate derived from the voltage measurement (again, assuming the uncertainty value is expressed as a percentage of the battery charge level).

If the minimum charge level estimate from the first charge level estimate is less than the minimum charge level estimate from the second charge level estimate (YES of 66), processor 10 may adjust the first charge level estimate based on the minimum charge level estimate from the second charge level estimate (68). To adjust the charge level estimate, processor 10 may sum the uncertainty value of the first charge level estimate with the minimum charge level estimate from the second charge level estimate.

After adjustment, in some cases, processor 10 may output the adjusted charge level estimate via telemetry module 16 for presentation of the adjusted charge level estimate (60). Again, it may not be necessary for processor 10 to output the adjusted charge level estimate for presentation in every example.

It should be noted that although block 62 is described as occurring before block 66, aspects of this disclosure are not so limited. In some examples, processor 10 may perform the functions described with respect to blocks 66, 68, and 60 before performing the functions described with respect to blocks 62, 64, and 60.

Furthermore, although FIG. 5 illustrates aspects of this disclosure where processor 10 uses two charge level estimates to adjust the charge level, aspects of this disclosure are not so limited. In some examples, processor 10 may use more than two charge level estimates, and their corresponding uncertainty values, to adjust the charge level utilizing techniques similar to those described above.

Figure 6:
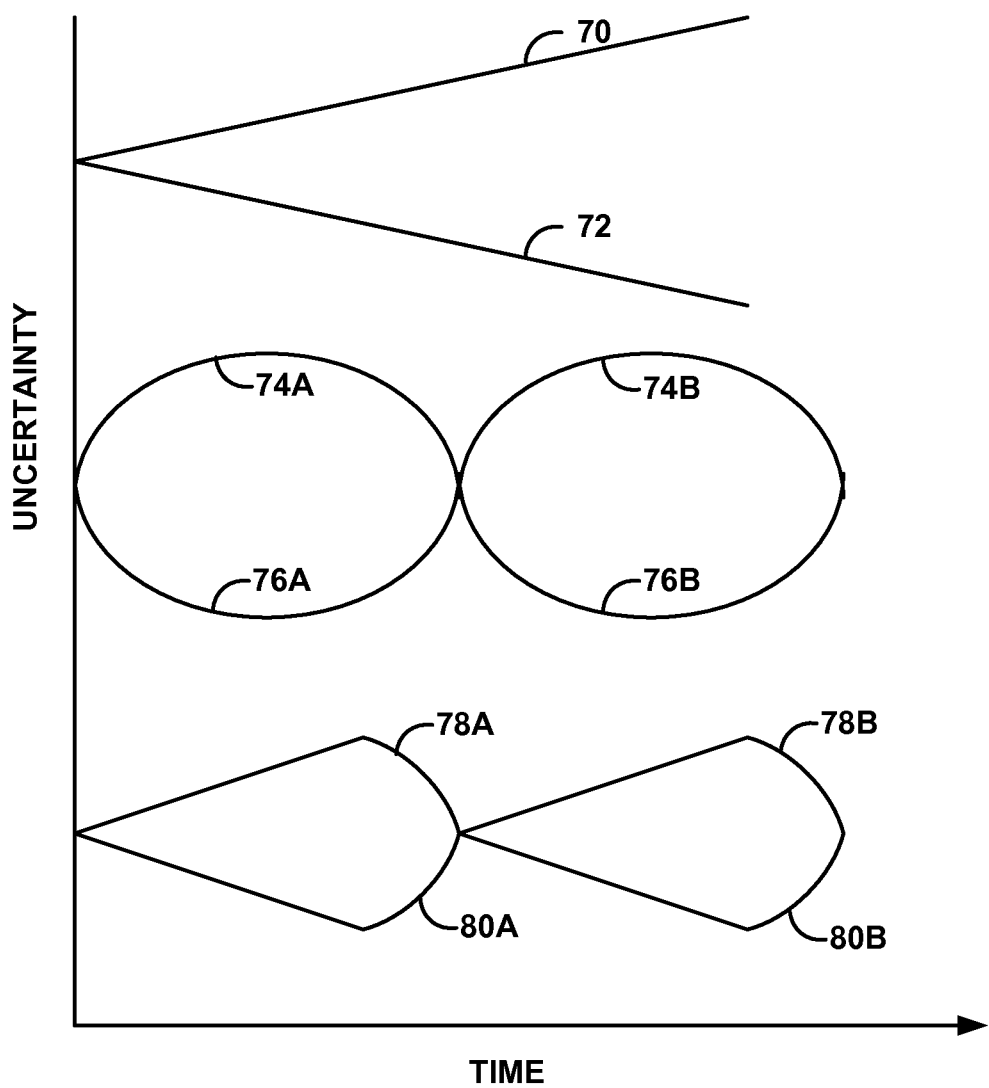
FIG. 6 is a graph illustrating an example of the uncertainty value of the adjusted charge level estimate.

FIG. 6 is a graph illustrating an example of the uncertainty value of the adjusted charge level estimate. It should be noted that FIG. 6 illustrates the uncertainty values of the charge level estimates and the adjusted charge level estimates. The adjusted charge level estimate itself may not directly track the example uncertainty values illustrated in FIG. 6.

In the example illustrated in FIG. 6, uncertainty value 70 indicates the positive uncertainty values of the charge level estimate derived from the measurement by coulomb counter 6 as a function of time, e.g., +10% uncertainty for a given time. Uncertainty value 72 indicates the negative uncertainty values of the charge level estimate derived from the measurement by coulomb counter 6 as a function of time, e.g., −10% uncertainty for a given time. Uncertainty value 74A indicates the positive uncertainty values of the charge level estimate derived from the measured voltage of power source 4 over a first discharge cycle. Uncertainty value 76A indicates the negative uncertainty value of the charge level estimate derived from the measured voltage of power source 4 over the first discharge cycle.

In the illustrated example of FIG. 6, power source 4 is initially at full charge, power source 4 then discharges over time, and is then recharged. Uncertainty value 74B indicates the positive uncertainty values of the charge level estimate derived from the measured voltage of power source 4 over a second discharge cycle. Uncertainty value 76B indicates the negative uncertainty values of the charge level estimate derived from the measured voltage of power source 4 over the second discharge cycle.

Uncertainty value 78A indicates the positive uncertainty values of the adjusted charge level estimate over the first discharge cycle. Uncertainty value 80A indicates the negative uncertainty values of the adjusted charge level estimate over the first discharge cycle. Uncertainty value 78B indicates the positive uncertainty values of the adjusted charge level estimate over the second discharge cycle. Uncertainty value 80B indicates the negative uncertainty values of the adjusted charge level estimates over the second discharge cycle.

As shown in FIG. 6, initially, the uncertainty of the charge level estimate derived from the measurement by coulomb counter 6 may be less than the uncertainty from the charge level estimate derived from the measured voltage. Accordingly, in these instances, the uncertainty value of the adjusted charge level estimate may be substantially the same as the uncertainty value of the charge level estimate derived from the measurement by coulomb counter 6, as illustrated in the examples of FIGS. 3B and 3C.

Over time, the uncertainty of the charge level estimate derived from the measurement by coulomb counter 6 may be greater than uncertainty from the charge level estimate derived from the measured voltage. Accordingly, in these instances, the uncertainty value of the adjusted charge level estimate may be substantially the same as the uncertainty value of the charge level estimate derived from the measured voltage, as illustrated in the example of FIG. 3A.

In some aspects of this disclosure, processor 10 may minimize the uncertainty of the charge level estimate derived from the measurement by coulomb counter 6, or some other technique to estimate charge level. For example, processor 10 may minimize the uncertainty of the charge level estimate to the smaller of the uncertainties between the charge level estimate derived from the measurement by coulomb counter 6 and the charge level estimate derived from the measured voltage of power source 4, as shown with respect to uncertainty values 78A, 78B, 80A, and 80B. In this manner, the adjusted charge level estimate may be a better estimation of the actual charge level with minimal uncertainty relative to the charge level estimate derived from the measurement by coulomb counter 6 or derived from the measured voltage of power source 4.

In some instances, the behavior of power source 4 may change over time. In some aspects of this disclosure, processor 10 may account for the changes in the behavior of power source 4 to readjust the adjusted charge level estimate.

There may be unit-to-unit variance, sometimes referred to as gamma factor, in the behavior of power source 4. For example, different power sources may be capable of providing different amounts of charge. Also, over time, there may be degrading of power source 4. After multiple charge and discharge cycles, the amount of charge that power source 4 may be capable of delivering may reduce. The reduction in the amount of charge that power source 4 can deliver may be caused by leakage, e.g., current-level drain, or due to impedance build up on power source 4. Moreover, in some instances, the actual amount of charge that power source 4 can deliver may be less than the amount of charge that power source 4 is designed to deliver.

In some instances, it may be possible for the charge level estimate derived from one technique to be different than the charge level estimate derived from another technique. FIGS. 3A-3C illustrate some examples of when the charge level estimate derived from the measurement by coulomb counter 6 is different than the charge level estimate derived from the measured voltage. The charge level estimate derived from the measured voltage may be different than the charge level estimate derived from the measurement by coulomb counter 6 because of changes in the behavior of power source 4.

While power source 4 is being recharged, coulomb counter 6 may increment its counter for every unit of charge that is delivered to power source 4. After power source 4 is fully charged, the total charge counted by coulomb counter 6 may indicate the total amount of charge that power source 4 can deliver. As described above, processor 10 may be programmed with the total amount of charge that power source 4 can deliver. However, due to changes in the behavior of power source 4 and drift in coulomb counter 6, the programmed total amount of charge of power source 4 may be different than the total amount of charge counted by coulomb counter 6.

Moreover, after power source 4 is fully charged, the voltage of power source 4 may be at its peak value even though the total amount of charge that power source 4 can deliver has reduced. As one example, when power source 4 is initially fully charged, power source 4 may be capable of delivering 100 mA-Hr, and the voltage of power source 4 may be 3 V. Over time, when power source 4 is later fully recharged, power source 4 may be capable of delivering 80 mA-Hr, and the voltage of power source 4 may be 3 V. Therefore, 100% of full capacity, may initially represent 100 mA-Hr of charge, and 100% of full capacity may later represent 80 mA-Hr of charge.

Figure 7:
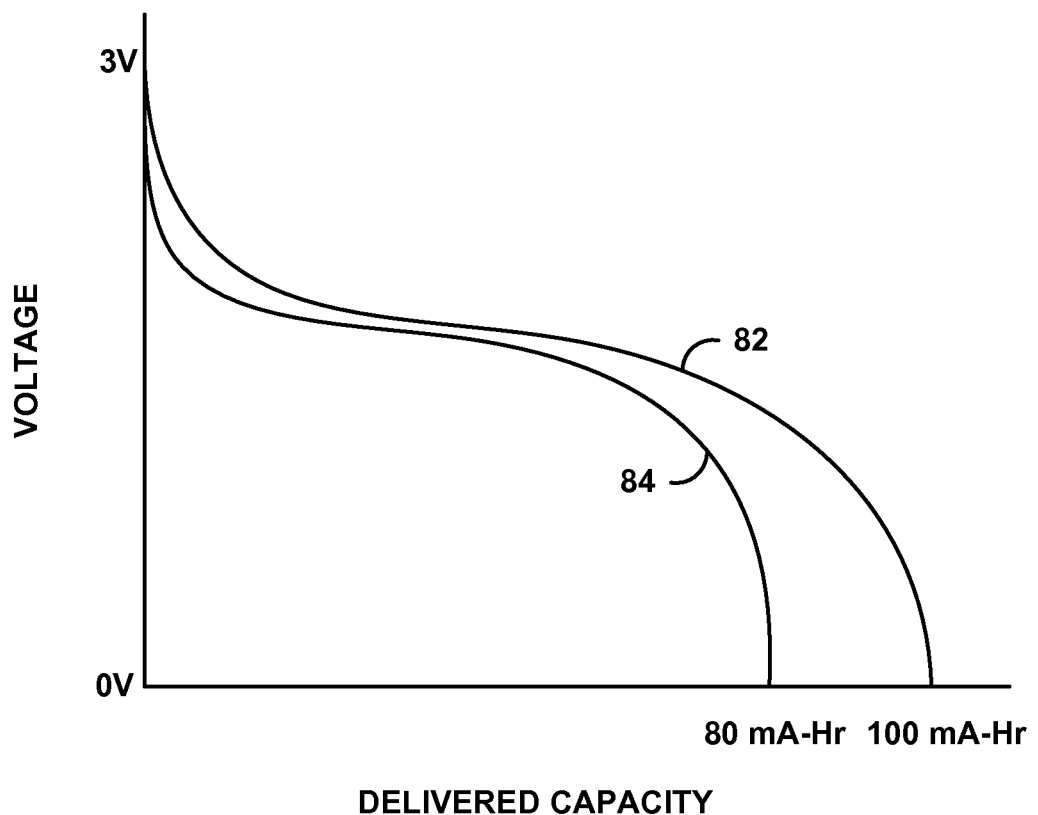
FIG. 7 is a graph illustrating an example of the reduction in the amount of charge that a power source can deliver over time during the course of power consumption by a device.

FIG. 7 is a graph illustrating an example of the reduction in the amount of charge that power source 4 can deliver over time during the course of power consumption by a device. Delivered capacity 82 indicates the voltage of power source 4 as a function of the amount of charge that power source 4 has delivered when power source 4 is relatively new, e.g., has not experienced multiple charge and discharge cycles. For example, delivered capacity 82 indicates that when power source 4 is fully discharged, power source 4 delivered 100 mA-Hr of charge. Accordingly, in the example illustrated in FIG. 7, when power source 4 is relatively new, power source 4 is capable of delivering 100 mA-Hr of charge.

Delivered capacity 84 indicates the voltage of power source 4 as a function of the amount of charge that power source 4 has delivered after power source 4 has been discharged and charged multiple times. For example, delivered capacity 84 indicates that when power source 4 is fully discharged, power source 4 delivered 80 mA-Hr of charge. Accordingly, over time power source 4 is capable of delivering 80 mA-Hr of charge when before power source 4 was capable of delivering 100 mA-Hr of charge.

Figure 8:
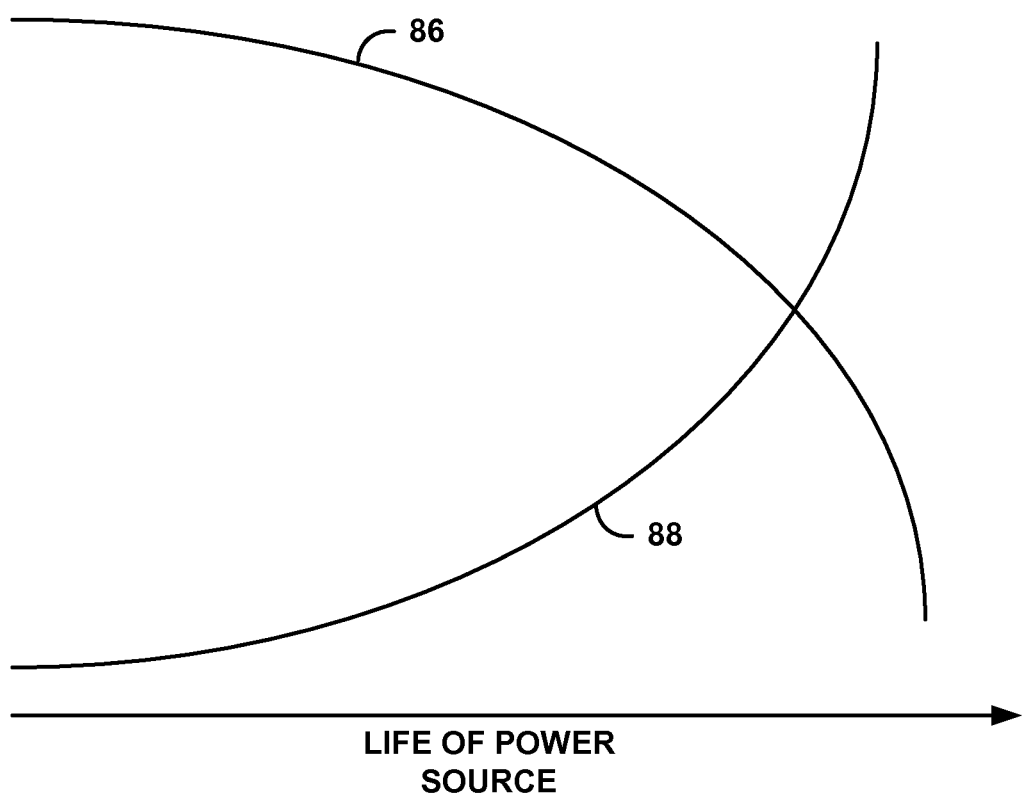
FIG. 8 is a graph illustrating the change in the amount of charge that a power source can deliver and the uncertainty value in the charge level estimate, derived from the voltage measurement, caused by the change in behavior of the power source as a function of time.

FIG. 8 is a graph illustrating the change in the amount of charge that power source 4 can deliver and the uncertainty value in the charge level estimate, derived from the voltage measurement, caused by the change in behavior of power source 4 as a function of time. Capacity 86 indicates that over the life of power source 4, the amount of charge that power source 4 can deliver decreases. In some instances, due to the changes in the behavior of power source 4, the uncertainty value of the charge level estimate derived from the measured voltage of power source 4 may increase over the life of power source 4, as indicated by uncertainty values 88. In some aspects of this disclosure, as described in more detail below, processor 10 may account for the changes in power source 4 to determine an even better approximation of the actual charge level of power source 4.

As described above, for example, with respect to FIG. 3B, if the maximum charge level estimate derived from the measurement by coulomb counter 6 is greater than the maximum charge level estimate derived from the measured voltage of power source 4, processor 10 may adjust the charge level estimate derived from the measurement by coulomb counter 6 to generate a bounded charge level estimate. Processor 10 may adjust the charge level derived from the measurement by coulomb counter 6 such that the maximum adjusted charge level estimate is substantially the same as the maximum charge level estimate derived from the measured voltage.

In some examples, processor 10 may further adjust the bounded charge level estimate to account for offsets caused by the changes in the behavior of power source 4. To further adjust the bounded charge level estimate, in some examples, processor 10 may compare the minimum charge level estimate from a first charge level estimate with the maximum charge level estimate from a second charge level estimate.

If the minimum charge level estimate from the first charge level estimate is greater than the maximum charge level estimate from the second charge level estimate, processor 10 may calculate the difference between the minimum charge level estimate from the first charge level estimate and the maximum charge level estimate from the second charge level estimate.

The difference between the two may be considered as the offset caused by the changes in the characteristics of power source 4. Processor 10 may subtract the offset from the bounded charge level estimate, e.g., the adjusted charge level estimate, to further adjust the adjusted charge level estimate.

As described above, the first and second charge level estimates may be derived from a measurement by coulomb counter 6, a voltage measurement, a pressure measurement, a temperature measurement, an impedance measurement, or a size measurement, measured by power source meter 8.

Figure 9A:
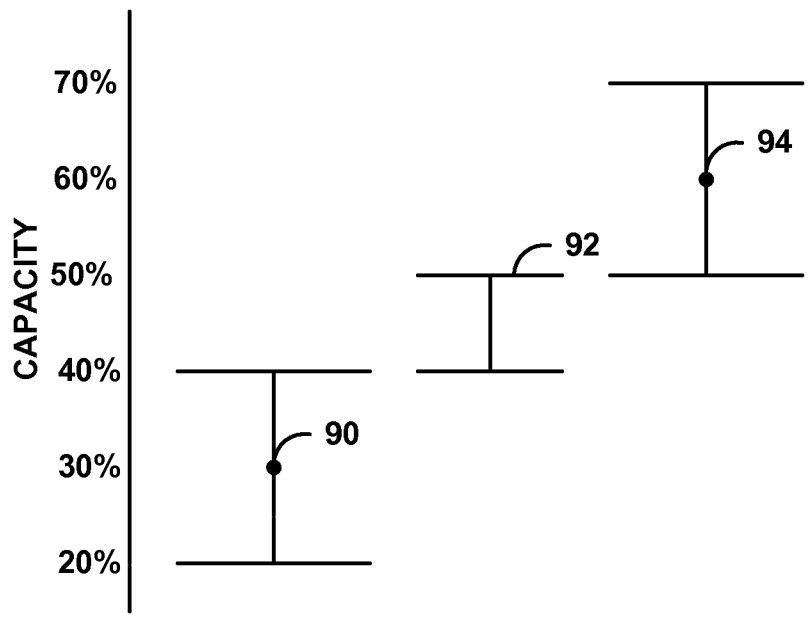
FIG. 9A is a diagram illustrating an example of a process for further adjusting an adjusted charge level estimate.

FIG. 9A is a diagram illustrating an example of a process for further adjusting an adjusted charge level estimate. For purposes of illustration, in FIG. 9A, the first charge level estimate is the charge level estimate derived from the measurement by coulomb counter 6 and the second charge level estimate is the charge level estimate derived from the voltage measurement. The example illustrated in FIG. 9A may be applicable when the minimum charge level estimate derived from the measurement by coulomb counter 6 is greater than the maximum charge level estimate from the measured voltage of power source 4. As one example, the example illustrated in FIG. 9A may be applicable after block 58 of FIG. 5 and before block 60 of FIG. 5.

Charge level estimate 90 indicates the charge level estimate derived from the measured voltage of power source 4. As one example, charge level estimate 90 is 30% of full capacity. Also, as one example, the maximum charge level estimate derived from the measured voltage of power source 4 is 40% of full capacity, as illustrated in FIG. 9A.

Charge level estimate 94 indicates the charge level estimate derived from the measurement by coulomb counter 6. As one example, charge level estimate 94 is 60% of full capacity. Also, as one example, the minimum charge level estimate derived from the measurement by coulomb counter 6 is 50% of full capacity.

In some examples, processor 10 may further adjust the bounded charge level estimate when the maximum charge level estimate derived from the measured voltage is less than the minimum charge level estimate derived from the measurement by coulomb counter 6. As one example, at block 64 of FIG. 5, processor 10 may adjust the charge level estimate from coulomb counter 6 to generate the bounded charge level estimate. In some examples, processor 10 may further adjust the bounded charge level estimate determined at block 64 of FIG. 5, as described in more detail below.

As illustrated in the example of FIG. 9A, the minimum charge level estimate derived from the measurement by coulomb counter 6 is greater than the maximum charge level estimate derived from the measured voltage of power source 4. In some of these instances, processor 10 may determine the difference, indicated as offset 92, between the minimum charge level estimate derived from the measurement by coulomb counter 6 and the maximum charge level estimate derived from the measured voltage.

Based on offset 92, processor 10 may further adjust the bounded charge level estimate. As one example, processor 10 may scale the bounded charge level estimate with offset 92 to further adjust the bounded charge level estimate. For example, as illustrated in the example of FIG. 9A, offset 92 is approximately 10%. To further adjust the bounded charge level estimate, processor 10 may subtract offset 92 from the bounded charge level estimate. In this manner, the resulting charge level estimate may account for changes in the behavior of power source 4. In some example, the resulting charge level estimate, e.g., the further adjusted bounded charge level estimate, may be referred to as an adaptive charge level estimate because the adaptive charge level estimate is adaptive to the changes in power source 4. In some instances, the adaptive charge level estimate may provide an even better approximation of the actual charge level as compared to the bounded charge level estimate, e.g., the adjusted charge level estimate from block 64.

As another example, as described above, for example, with respect to FIG. 3C, if the minimum charge level estimate from a first charge level estimate is less than the minimum charge level estimate from a second charge level estimate, processor 10 may adjust the first charge level estimate to generate a bounded charge level estimate. Processor 10 may adjust the first charge level estimate such that the minimum adjusted charge level estimate is substantially the same as the minimum charge level estimate from the second charge level estimate.

In some of these instances, to account for offsets caused by changes in the behavior of power source 4, processor 10 may compare the maximum charge level estimate from the first charge level estimate with the minimum charge level estimate from the second charge level estimate. If the maximum charge level estimate from the first charge level estimate is less than the minimum charge level estimate from the second charge level estimate, processor 10 may calculate the difference between the maximum charge level estimate from the first charge level estimate and the minimum charge level estimate from the second charge level estimate. As described above, the first and second charge level estimates may be derived from a measurement by coulomb counter 6, a voltage measurement, a pressure measurement, a temperature measurement, an impedance measurement, or a size measurement, measured by power source meter 8.

The difference between the two may be considered as the offset caused by the changes in the behavior of power source 4. In some of these instances, processor 10 may add the offset from the bounded charge level estimate, e.g., the adjusted charge level estimate, to further adjust the adjusted charge level estimate.

Figure 9B:
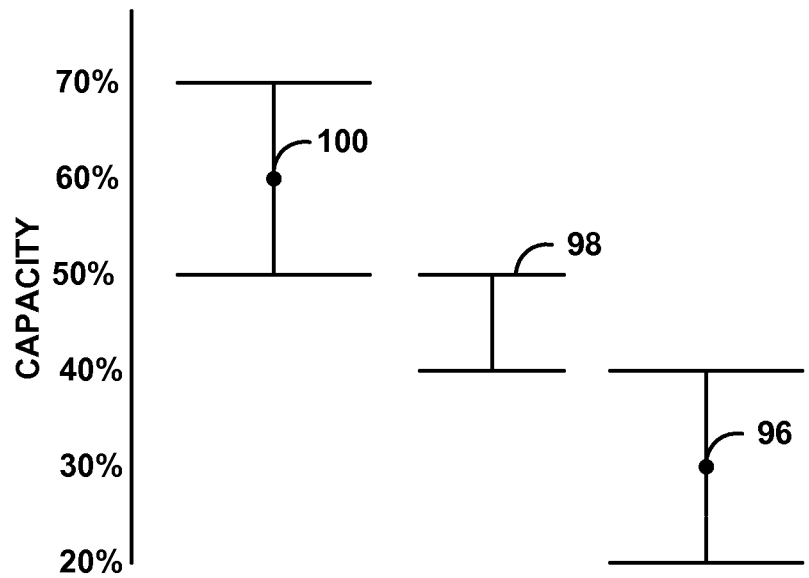
FIG. 9B is a diagram illustrating another example of a process for further adjusting an adjusted charge level estimate.

FIG. 9B is a diagram illustrating another example of a process for further adjusting an adjusted charge level estimate. For purposes of illustration, in FIG. 9B, the first charge level estimate is the charge level estimate derived from the measurement by coulomb counter 6 and the second charge level estimate is the charge level estimate derived from the voltage measurement. The example illustrated in FIG. 9B may be applicable when the maximum charge level estimate derived from the measurement by coulomb counter 6 is less than the minimum charge level estimate derived from the measured voltage of power source 4. As one example, the example illustrated in FIG. 9B may be applicable after block 68 of FIG. 5.

Charge level estimate 100 indicates the charge level estimate derived from the measured voltage of power source 4. As one example, charge level estimate 100 is 60% of full capacity. Also, as one example, the minimum charge level estimate derived from the measured voltage of power source 4 is 50% of full capacity, as illustrated in FIG. 9B.

Charge level estimate 96 indicates the charge level estimate derived from the measurement by coulomb counter 6. As one example, charge level estimate 96 is 30% of full capacity. Also, as one example, the maximum charge level estimate derived from the measurement by coulomb counter 6 is 40% of full capacity.

In some examples, processor 10 may further adjust the bounded charge level estimate when the minimum charge level derived from the measured voltage is greater than the maximum charge level derived from the measurement by coulomb counter 6. As one example, at block 68 of FIG. 5, processor 10 may adjust the charge level estimate derived from the measurement by coulomb counter 6 to generate the bounded charge level estimate. In some examples, processor 10 may further adjust the bounded charge level estimate determined at block 68, as described in more detail below.

As illustrated in the example of FIG. 9B, the maximum charge level estimate derived from the measurement by coulomb counter 6 is less than the minimum charge level estimate derived from the measured voltage of power source 4. In some of these instances, processor 10 may determine the difference, indicated as offset 98, between the maximum charge level estimate derived from the measurement by coulomb counter 6 and the minimum charge level estimate derived from the measured voltage.

Based on offset 98, processor 10 may further adjust the bounded charge level estimate. As one example, processor 10 may scale the bounded charge level estimate with offset 98 to further adjust the bounded charge level estimate. For example, as illustrated in the example of FIG. 9B, offset 98 is approximately 10%. To further adjust the bounded charge level estimate, processor 10 may sum offset 98 with the bounded charge level estimate. In this manner, the resulting charge level estimate may account for changes in the behavior of power source 4. In some example, the resulting charge level estimate, e.g., the further adjusted bounded charge level estimate, may be referred to as an adaptive charge level estimate. In some instances, the adaptive charge level estimate may provide an even better approximation of the actual charge level, of power source 4, as compared to the bounded charge level estimate, e.g., the adjusted charge level from block 68 of FIG. 5.

Figure 10:
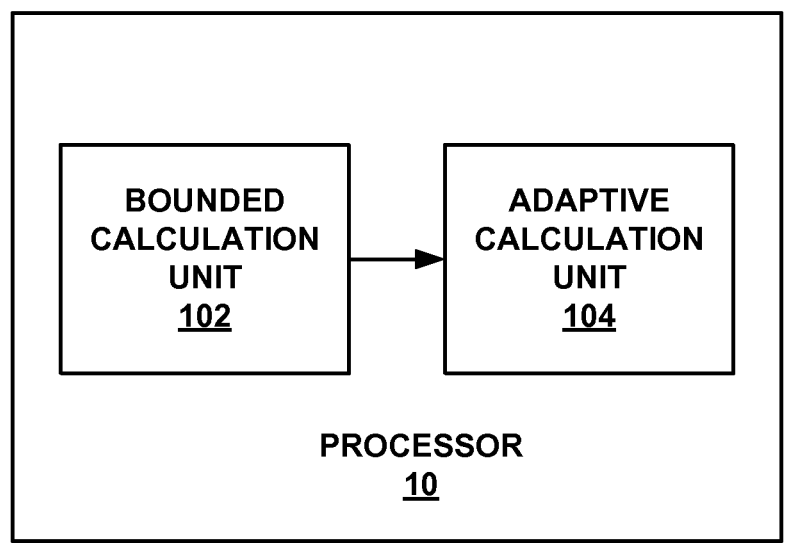
FIG. 10 is a block diagram illustrating functional components of the processor of FIG. 1 in further detail.

FIG. 10 is a block diagram illustrating functional components of the processor 10 in further detail. Processor 10 may include bounded calculation unit 102 and adaptive calculation unit 102. Units 102 and 104 may be implemented in hardware or a combination of hardware and software.

Bounded calculation unit 102 may calculate the bounded charge level in accordance with techniques described above. Adaptive calculation unit 104 may calculate the adaptive charge level in accordance with techniques described above. It should be noted that units 102 and 104 may not be necessary in every example of processor 10. In some examples, processor 10 may be configured to calculate the bounded charge level, and not be configured to calculate the adaptive charge level. In these examples, processor 10 may include bounded calculation unit 102 and may not include adaptive calculation unit 142.

Figure 11:
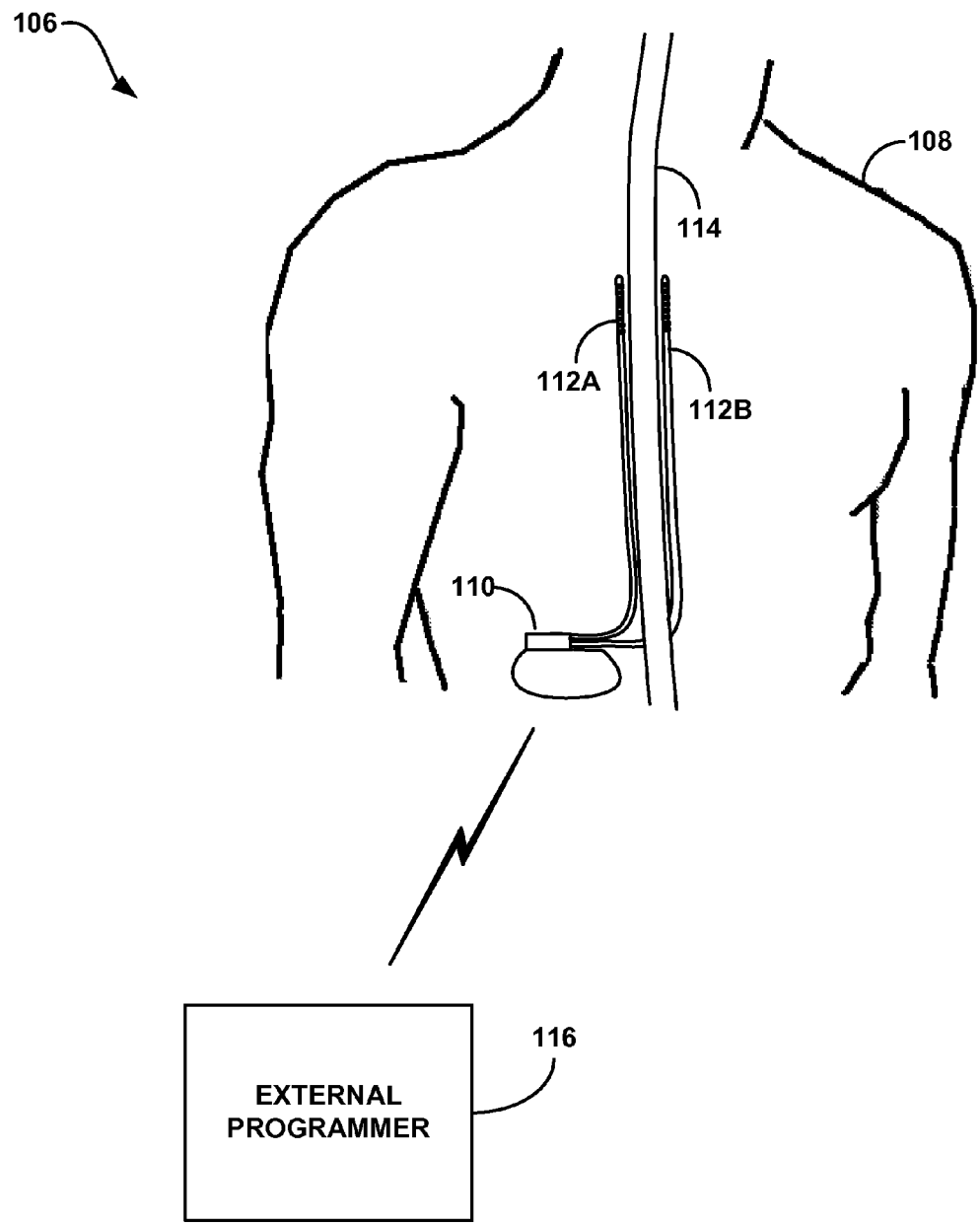
FIG. 11 is a schematic diagram illustrating an implantable medical device (IMD) system including an IMD and an external programmer.

FIG. 11 is a schematic diagram illustrating an implantable medical device (IMD) system including an IMD and an external programmer. As shown in FIG. 11, system 106 includes an implantable device 110 and an external programmer 116 shown in conjunction with patient 108. Implantable device 110 may be similar to device 2 (FIG. 1). Although FIG. 11 shows an implantable device 110 coupled to fully implanted leads 112A, 112B, the techniques described in this disclosure may be applied to external stimulators coupled to leads via percutaneous lead extensions.

As shown in FIG. 11, leads 112A, 112B are implanted adjacent a spinal cord 114 of patient 108, e.g., for spinal cord stimulation (SCS) to alleviate pain. However, the techniques described in this disclosure are applicable to leads implanted to target any of a variety of target locations within patient 108, such as leads carrying electrodes located proximate to spinal cord 114, pelvic nerves, peripheral nerves, the stomach or other gastrointestinal organs, or within the brain of a patient. Also, techniques of this disclosure are applicable to other IMDs, such as those that deliver substances, e.g., drugs, to a patient.

In the example of FIG. 11, stimulation energy is delivered from device 110 to spinal cord 114 of patient 108 via one or more electrodes carried by axial leads 112A and 112B (collectively "leads 112") implanted within the patient. In various applications, such as spinal cord stimulation (SCS), the adjacent implantable leads 112 may have longitudinal axes that are substantially parallel to one another. Various combinations of electrodes carried by the leads 112 may be used to deliver electrical stimulation, including combinations of electrodes on a single lead or combinations of electrodes on both leads. Also, in some examples, electrodes may be carried by paddle leads in which an array of electrodes may be arranged in a two-dimensional pattern, e.g., as columns or rows of electrodes, on a common planar lead surface.

In the example of FIG. 11, leads 112 carry electrodes that are placed adjacent to the target tissue of spinal cord 114. In particular, leads 112 may be implanted in the epidural space adjacent spinal cord 114, and coupled to an implanted device 110. In the example of FIG. 11, stimulation energy may be delivered to spinal cord 114 to eliminate or reduce pain perceived by patient 108. However, device 110 may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, epilepsy, urinary or fecal incontinence, sexual dysfunction, obesity, or gastroparesis. The stimulation delivered by device 110 may take the form of stimulation pulses or continuous waveforms, and may be characterized by controlled voltage levels or controlled current levels, as well as pulse width and pulse rate in the case of stimulation pulses.

A user, such as a clinician, physician or patient 108, may interact with a user interface of external programmer 116 to program stimulator 110. Programming of device 116 may refer generally to the generation and transfer of commands, programs, or other information to control the operation of device 110. For example, programmer 116 may transmit programs, parameter adjustments, program selections, group selections, or other information to control the operation of device 110, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

As described above, in some examples, the functionality ascribed to processor 10 of device 2 may be performed by devices other than device 2. In some examples, external programmer 116 may include a processor substantially similar to processor 10. The processor of external programmer 116 may be configured to perform functions similar to those described above with respect to processor 10.

In some cases, external programmer 116 may be a physician or clinician programmer if it is primarily intended for use by a physician or clinician. In other cases, external programmer 116 may be a patient programmer if it is primarily intended for use by a patient. In general, a physician or clinician programmer may support selection and generation of programs or parameters by a clinician for use by device 110, whereas a patient programmer may support more limited adjustment and selection of such programs or parameters by a patient during ordinary use.

Device 110 may be implanted in patient 108 at a location minimally noticeable to the patient. Alternatively, the device may be external to patient 108 and coupled to implanted leads via a percutaneous extension. For spinal cord stimulation (SCS), as an example, device 110 may be located, for example, in the lower abdomen, lower back, or other location to secure the stimulator. Leads 112 may be tunneled from device 110 through tissue to reach the target tissue adjacent to spinal cord 114 for stimulation delivery. At distal portions of leads 112 are one or more electrodes (not shown) that transfer stimulation energy from the lead to the tissue. The electrodes may be electrode pads on a paddle lead, circular (i.e., ring)

electrodes, surrounding the body of leads 112, segmented electrodes arranged at different axial and rotational positions around a lead, conformable electrodes, cuff electrodes, or any other type of electrodes capable of forming unipolar, bipolar or multipolar electrode configurations.

The techniques described in this disclosure, including those attributed to processor 10, coulomb counter 6, power source meter 8, A/D converter 14, timer 18, or various constituent components, may be implemented, at least in part, in hardware, software, firmware or any combination thereof. For example, various aspects of the techniques may be implemented within one or more processors, e.g., processor 10, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

In general, the techniques described in this disclosure can be applied to devices that are powered by one or more power sources such as batteries or capacitors. The techniques may be applied to medical devices such implantable medical devices configured to deliver neurostimulation or other electrical stimulation therapy via implanted electrode arrays, carried by leads or otherwise, located proximate to the spinal cord, pelvic nerves, peripheral nerves, the stomach or other gastrointestinal organs, or within the brain of a patient. The techniques described in this disclosure can be applied to medical devices that may not include electrodes to provide electrical stimulation. For examples, the techniques described in this disclosure can be applied to medical devices that provide medication in accordance with a delivery schedule. The techniques described in this disclosure may also be applied to medical devices that are external to the patient, as well as medical devices that used to program other medical devices. The techniques described in this disclosure may also be applied to non-medical devices such as laptop computers, gaming counsels, mobile phones, personal digital assistants (PDAs), and other such devices.

Many aspects of the disclosure have been described. Various modifications may be made without departing from the scope of the claims. These and other aspects are within the scope of the following claims.

The invention claimed is:

1. A method comprising:
measuring a first estimated value of a charge level of a power source associated with a medical device using a first unit;
measuring a second estimated value of the charge level of the power source using a second unit;
determining, with a processor, a first margin of uncertainty associated with the first estimated value of the charge level of the power source and a second margin of uncertainty associated with the second estimated value of the charge level of the power source;
at least one of:
 determining a first value based on an addition of the first margin of uncertainty to the first estimated value of the charge level, and a second value based on an addition of the second margin of uncertainty to the second estimated value of the charge level; or
 determining a third value based on a subtraction of the first margin of uncertainty from the first estimated value of the charge level, and a fourth value based on a subtraction of the second margin of uncertainty from the second estimated value of the charge level;
at least one of comparing the first value and the second value or comparing the third value and the fourth value; and
adjusting, with the processor, the first estimated value of the charge level based on at least the comparison to generate an adjusted estimated value of the charge level.

2. The method of claim 1, wherein the first unit and the second unit are different, and wherein the first estimated value of the charge level comprises one of a charge level value derived from a measurement by a coulomb counter, or a charge level value derived from one of a voltage, pressure, temperature, impedance, or size of the power source, and wherein the second estimated value of the charge level comprises one of a charge level value derived from the measurement by the coulomb counter, or the charge level value derived from one of the voltage, pressure, temperature, impedance, or size of the power source, and that is different from the first estimated value of the charge level.

3. The method of claim 1, further comprising:
determining a third margin of uncertainty associated with a third estimated value of the charge level of the power source,
wherein adjusting the first estimated value of the charge level comprises adjusting the first estimated value of the charge level based on at least the comparison and the third margin of uncertainty to generate the adjusted estimated value of the charge level.

4. The method of claim 1, wherein each of the first and second estimated values of the charge level and the adjusted estimated value of the charge level indicate an amount of charge remaining on the power source.

5. The method of claim 1, wherein each of the first and second estimated values of the charge level and the adjusted estimated value of the charge level indicate a percentage of charge remaining on the power source.

6. The method of claim 1, wherein each of the first and second estimated values of the charge level and the adjusted estimated value of the charge level indicate a remaining amount of operation time of the power source.

7. The method of claim 1, wherein determining the first margin of uncertainty comprises determining the first margin of uncertainty based on a stored indication of the first margin of uncertainty, and wherein determining the second margin of uncertainty comprises determining the second margin of uncertainty based on a stored indication of the second margin of uncertainty.

8. The method of claim 1, further comprising:
determining whether the first value is greater than the second value based on the comparison;
determining a first minimum value based on the first estimated value of the charge level and the first margin of uncertainty when the first value is greater than the second value;
comparing the first minimum value with the second value when the first value is greater than the second value; and
further adjusting the adjusted estimated value of the charge level based on the comparison of the first minimum value with the second value.

9. The method of claim 1, further comprising:
determining whether the third value is less than the fourth value;
determining a first maximum value based on the first estimated value and the first margin of uncertainty when the third value is less than the fourth value;
comparing the first maximum value with the fourth value when the third value is less than the fourth value; and
further adjusting the adjusted estimated value of the charge level based on the comparison of the first maximum value with the fourth value.

10. The method of claim 1, further comprising:
transmitting the adjusted estimated value of the charge level for presentation.

11. The method of claim 1, further comprising:
subtracting a margin of uncertainty associated with the adjusted estimated value of the charge level from the adjusted estimated value of the charge level to generate a minimum value of the adjusted estimated value of the charge level; and
transmitting the minimum value of the adjusted estimated value of the charge level for presentation.

12. The method of claim 1, wherein determining the third value and the fourth value comprises determining the third value and the fourth value if the first value is less than the second value, and wherein comparing the third value and the fourth value comprises comparing the third value and the fourth value if the first value is less than the second value.

13. A medical device system comprising:
a power source;
a measurement unit configured to measure a first estimated value of a charge level of the power source and a second estimated value of the charge level of the power source; and
a processor configured to:
determine a first margin of uncertainty associated with the first estimated value of the charge level of the power source and a second margin of uncertainty associated with the second estimated value of the charge level of the power source;
at least one of:
determine a first value based on an addition of the first margin of uncertainty to the first estimated value of the charge level, and a second value based on an addition of the second margin of uncertainty to the second estimated value of the charge level; or
determine a third value based on a subtraction of the first margin of uncertainty from the first estimated value of the charge level, and a fourth value based on a subtraction of the second margin of uncertainty from the second estimated value of the charge level;
at least one of compare the first value and the second value or compare the third value and the fourth value; and
adjust the first estimated value of the charge level based on at least the comparison to generate an adjusted estimated value of the charge level.

14. The system of claim 13, wherein the measurement unit comprises a first unit and a second, different unit, wherein the first estimated value of the charge level is measured by the first unit and comprises one of a charge level derived from a measurement by a coulomb counter, or a charge level derived from one of a voltage, pressure, temperature, impedance, or size of the power source, and wherein the second estimated value of the charge level is measured by the second unit and comprises one of a charge level value derived from the measurement by the coulomb counter, or the charge level value derived from one of the voltage, pressure, temperature, impedance, or size of the power source, and that is different from the first estimated value of the charge level.

15. The system of claim 13, wherein the processor is further configured to:
determine a third margin of uncertainty associated with a third estimated value of the charge level of the power source,
wherein the processor is configured to adjust the first estimated value of the charge level based on at least the comparison and the third margin of uncertainty to generate the adjusted estimated value of the charge level.

16. The system of claim 13, wherein each of the first and second estimated values of the charge level and the adjusted estimated value of the charge level indicate an amount of charge remaining on the power source.

17. The system of claim 13, wherein each of the first and second estimated values of the charge level and the adjusted estimated value of the charge level indicate a percentage of charge remaining on the power source.

18. The system of claim 13, wherein each of the first and second estimated values of the charge level and the adjusted estimated value of the charge level indicate a remaining amount of operation time of the power source.

19. The system of claim 13, further comprising an implantable medical device (IMD), wherein the IMD includes the power source, the measurement unit, and the processor.

20. The system of claim 13, further comprising an implantable medical device (IMD), and a programmer, wherein the programmer includes the processor, and wherein the IMD includes the power source, and the measurement unit.

21. The system of claim 13, wherein the processor is configured to determine the first margin of uncertainty based on a stored indication of the first margin of uncertainty, and wherein the processor is configured to determine the second margin of uncertainty based on a stored indication of the second margin of uncertainty.

22. The system of claim 13, wherein the processor is further configured to:
determine whether the first value is greater than the second value;
determine a first minimum value based on the first estimated value of the charge level and the first margin of uncertainty when the first value is greater than the second value;
compare the first minimum value with the second value when the first value is greater than the second value; and further adjust the adjusted estimated value of the charge level based on the comparison of the first minimum value with the second value.

23. The system of claim 13, wherein the processor is further configured to:
   determine whether the third value is less than the fourth value;
   determine a first maximum value based on the first estimated value and the first margin of uncertainty when the third value is less than the fourth value;
   compare the first maximum value with the fourth value when the third value is less than the fourth value; and
   further adjust the adjusted estimated value of the charge level based on the comparison of the first maximum value with the fourth value.

24. The system of claim 13, further comprising:
   a telemetry module configured to transmit the adjusted estimated value of the charge level for presentation.

25. The system of claim 13, further comprising:
   a telemetry module,
   wherein the processor is further configured to subtract a margin of uncertainty associated with the adjusted estimated value of the charge level from the adjusted estimated value of the charge level to generate a minimum value of the adjusted estimated value of the charge level, and
   wherein the telemetry module is configured to transmit the minimum value of the adjusted estimated value of the charge level for presentation.

26. The system of claim 13, wherein the processor is configured to determine the third value and the fourth value if the first value is less than the second value, and wherein the processor is configured to compare the third value and the fourth value if the first value is less than the second value.

27. The system of claim 13, further comprising a programmer, wherein the programmer includes the power source, the first unit, the second unit, and the processor.

28. A non-transitory computer-readable storage medium comprising instructions that cause one or more processors in a medical device to:
   receive a first estimated value of a charge level of a power source associated with the medical device from a first unit;
   receive a second estimated value of the charge level of the power source associated with the medical device from a second unit;
   determine a first margin of uncertainty associated with the first estimated value of the charge level of the power source and a second margin of uncertainty associated with the second estimated value of the charge level of the power source;
   at least one of:
      determine a first value based on an addition of the first margin of uncertainty to the first estimated value of the charge level, and a second value based on an addition of the second margin of uncertainty to the second estimated value of the charge level; or
      determine a third value based on a subtraction of the first margin of uncertainty from the first estimated value of the charge level, and a fourth value based on a subtraction of the second margin of uncertainty from the second estimated value of the charge level;
   at least one of compare the first value and the second value or compare the third value and the fourth value; and
   adjust the first estimated value of the charge level based on at least the comparison to generate an adjusted estimated value of the charge level.

* * * * *